United States Patent
Bertaud et al.

(10) Patent No.: US 11,844,828 B2
(45) Date of Patent: Dec. 19, 2023

(54) VACCINE

(71) Applicant: GLAXOSMITHKLINE BIOLOGICALS, SA, Rixensart (BE)

(72) Inventors: Elisabeth Marie Monique Bertaud, Rixensart (BE); Ralph Leon Biemans, Rixensart (BE); Nicolas Jean Benoit Moniotte, Rixensart (BE); Laurent Bernard Jean Strodiot, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/769,542

(22) PCT Filed: Oct. 19, 2016

(86) PCT No.: PCT/EP2016/075045
§ 371 (c)(1),
(2) Date: Apr. 19, 2018

(87) PCT Pub. No.: WO2017/067962
PCT Pub. Date: Apr. 27, 2017

(65) Prior Publication Data
US 2018/0303923 A1    Oct. 25, 2018

(30) Foreign Application Priority Data
Oct. 21, 2015  (GB) ..................... 1518684

(51) Int. Cl.
*A61K 47/64*   (2017.01)
*A61K 39/09*   (2006.01)
*A61K 39/00*   (2006.01)

(52) U.S. Cl.
CPC .......... *A61K 39/092* (2013.01); *A61K 47/646* (2017.08); *A61K 47/6415* (2017.08); *A61K 2039/6087* (2013.01); *A61K 2039/70* (2013.01)

(58) Field of Classification Search
CPC ....... A61K 39/00; A61K 39/02; A61K 39/092
USPC ....... 424/184.1, 193.1, 197.11, 203.1, 234.1, 424/237.1
See application file for complete search history.

(56) References Cited

U.S. PATENT DOCUMENTS

| | | | |
|---|---|---|---|
| 2010/0209450 A1* | 8/2010 | Biemans | A61K 39/092 424/197.11 |
| 2011/0019086 A1 | 1/2011 | Almeida et al. | |
| 2012/0321658 A1* | 12/2012 | Biemans | A61P 43/00 530/395 |
| 2015/0202309 A1 | 7/2015 | Emini et al. | |

FOREIGN PATENT DOCUMENTS

| | | | | |
|---|---|---|---|---|
| CN | 101785857 B | 9/2012 | | |
| CN | 103830723 A | 6/2014 | | |
| JP | 2010-531330 A | 9/2010 | | |
| JP | 2014205673 A | 10/2014 | | |
| WO | WO09000826 | * | 12/2006 | |
| WO | 2007/071707 A2 | 6/2007 | | |
| WO | 2007071710 A2 | 6/2007 | | |
| WO | WO07071707 | * | 6/2007 | |
| WO | 2009/000826 A1 | 12/2008 | | |
| WO | 2009000825 A2 | 12/2008 | | |
| WO | 2011/110241 A1 | 9/2011 | | |
| WO | WO2011/110241 | * | 9/2011 | ............ A61K 39/09 |
| WO | WO11110241 | * | 9/2011 | |
| WO | 2014/060383 A1 | 4/2014 | | |
| WO | WO14060383 | * | 4/2014 | |
| WO | 2017067962 A1 | 4/2017 | | |

OTHER PUBLICATIONS

Zhang, et al., "Comparison of methods for determination of molecular size and molecular weight of pneumococcal capsular polysaccharides." Chinese Journal of Biologicals; 2015; pp. 947-960; vol. 28, Issue 9.

* cited by examiner

*Primary Examiner* — S. Devi

(57) ABSTRACT

The present invention is in the field of pneumococcal capsular saccharide conjugate vaccines. Specifically, the present invention relates to sized *Streptococcus pneumoniae* serotype 6A capsular polysaccharides, in particular *Streptococcus pneumoniae* serotype 6A capsular polysaccharides having the average size (e.g. $M_w$) of the *Streptococcus pneumoniae* serotype 6A capsular polysaccharide is between 100-1000 kDa, suitably conjugated to a carrier protein.

17 Claims, 4 Drawing Sheets
Specification includes a Sequence Listing.

Figure 1: Evaluation of PS6A conjugates in 14V AlPO4 formulation in the Balb/c mouse with co-administration of Infanrix Hexa model. ELISA anti-PS6A.

(A)

(B)

SEQUENCE LISTING

<160> NUMBER OF SEQ ID NOS: 4

<210> SEQ ID NO 1
<211> LENGTH: 364
<212> TYPE: PRT
<213> ORGANISM: Haemophilus influenzae

<400> SEQUENCE: 1

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
                20                  25                  30

Ser Asp Lys Ile Ile Ile Ala His Arg Gly Ala Ser Gly Tyr Leu Pro
            35                  40                  45

Glu His Thr Leu Glu Ser Lys Ala Leu Ala Phe Ala Gln Gln Ala Asp
        50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
        115                 120                 125

Asp Gly Lys Gln Ala Gln Val Tyr Pro Asn Arg Phe Pro Leu Trp Lys
    130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220

Glu Leu Leu Pro Gln Met Gly Met Asp Leu Lys Leu Val Gln Leu Ile
225                 230                 235                 240

```
Ala Tyr Thr Asp Trp Lys Glu Thr Gln Glu Lys Asp Pro Lys Gly Tyr
            245                 250                 255

Trp Val Asn Tyr Asn Tyr Asp Trp Met Phe Lys Pro Gly Ala Met Ala
        260                 265                 270

Glu Val Val Lys Tyr Ala Asp Gly Val Gly Pro Gly Trp Tyr Met Leu
        275                 280                 285

Val Asn Lys Glu Glu Ser Lys Pro Asp Asn Ile Val Tyr Thr Pro Leu
        290                 295                 300

Val Lys Glu Leu Ala Gln Tyr Asn Val Glu Val His Pro Tyr Thr Val
305                 310                 315                 320

Arg Lys Asp Ala Leu Pro Glu Phe Phe Thr Asp Val Asn Gln Met Tyr
                325                 330                 335

Asp Ala Leu Leu Asn Lys Ser Gly Ala Thr Gly Val Phe Thr Asp Phe
                340                 345                 350

Pro Asp Thr Gly Val Glu Phe Leu Lys Gly Ile Lys
            355                 360
```

<210> SEQ ID NO 2
<211> LENGTH: 348
<212> TYPE: PRT
<213> ORGANISM: Haemophilus influenzae

<400> SEQUENCE: 2

```
Met Asp Pro Ser Ser His Ser Ser Asn Met Ala Asn Thr Gln Met Lys
1               5                   10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Lys
            100                 105                 110

Asp Gly Lys Gln Ala Gln Val Tyr Pro Asn Arg Phe Pro Leu Trp Lys
        115                 120                 125

Ser His Phe Arg Ile His Thr Phe Glu Asp Glu Ile Glu Phe Ile Gln
    130                 135                 140

Gly Leu Glu Lys Ser Thr Gly Lys Lys Val Gly Ile Tyr Pro Glu Ile
145                 150                 155                 160

Lys Ala Pro Trp Phe His His Gln Asn Gly Lys Asp Ile Ala Ala Glu
                165                 170                 175

Thr Leu Lys Val Leu Lys Lys Tyr Gly Tyr Asp Lys Lys Thr Asp Met
            180                 185                 190

Val Tyr Leu Gln Thr Phe Asp Phe Asn Glu Leu Lys Arg Ile Lys Thr
        195                 200                 205

Glu Leu Leu Pro Gln Met Gly Met Asp Leu Lys Val Gln Leu Ile
    210                 215                 220

Ala Tyr Thr Asp Trp Lys Glu Thr Gln Glu Lys Asp Pro Lys Gly Tyr
225                 230                 235                 240

Trp Val Asn Tyr Asn Tyr Asp Trp Met Phe Lys Pro Gly Ala Met Ala
```

```
                        245                 250                 255
Glu Val Val Lys Tyr Ala Asp Gly Val Gly Pro Gly Trp Tyr Met Leu
            260                 265                 270

Val Asn Lys Glu Glu Ser Lys Pro Asp Asn Ile Val Tyr Thr Pro Leu
        275                 280                 285

Val Lys Glu Leu Ala Gln Tyr Asn Val Glu Val His Pro Tyr Thr Val
    290                 295                 300

Arg Lys Asp Ala Leu Pro Glu Phe Phe Thr Asp Val Asn Gln Met Tyr
305                 310                 315                 320

Asp Ala Leu Leu Asn Lys Ser Gly Ala Thr Gly Val Phe Thr Asp Phe
                325                 330                 335

Pro Asp Thr Gly Val Glu Phe Leu Lys Gly Ile Lys
                340                 345

<210> SEQ ID NO 3
<211> LENGTH: 10
<212> TYPE: PRT
<213> ORGANISM: Haemophilus influenzae

<400> SEQUENCE: 3

Ser Ser His Ser Ser Asn Met Ala Asn Thr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Type 1
      Signal Motif
<220> FEATURE:
<221> NAME/KEY: misc_feature
<222> LOCATION: (3)..(3)
<223> OTHER INFORMATION: Xaa can be any amino acid

<400> SEQUENCE: 4

Leu Pro Xaa Thr Gly
1               5
```

VACCINE

CROSS-REFERENCE TO RELATED APPLICATIONS

This application is filed pursuant to 35 U.S.C. § as a United States National Phase Application of International Application No. PCT/EP2016/075045, filed Oct. 19, 2016 which claims priority from GB1518684.4 filed Oct. 21, 2015.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: VB65979_seq_list ST25.txt; created Apr. 14, 2023, size: 6,872 bytes).

FIELD OF THE INVENTION

The present invention relates to sized *Streptococcus pneumoniae* serotype 6A capsular polysaccharides, in particular *Streptococcus pneumoniae* serotype 6A capsular polysaccharides having an average size (e.g. $M_w$) between 100-1000, 110-750, 150-500, 180-600, 210-490, 210-450, 180-400, 210-400, 210-370, 220-360, 230-350, 240-340, 240-320, 240-310 or 250-310 kDa. It additionally relates to sized *Streptococcus pneumoniae* serotype 6A capsular polysaccharides conjugated to a carrier protein, immunogenic compositions, vaccines and processes for making the sized *Streptococcus pneumoniae* serotype 6A capsular polysaccharides. It also relates to the use of the immunogenic compositions and vaccines of the invention in therapy and methods of immunising against *Streptococcus pneumoniae* infection.

BACKGROUND OF THE INVENTION

*Streptococcus pneumoniae* (*S. pneumoniae*) is a Gram-positive bacterium responsible for considerable morbidity and mortality (particularly in infants and the elderly), causing invasive diseases such as bacteraemia and meningitis, pneumonia and other non-invasive diseases, such as acute otitis media. About 800,000 children die annually due to pneumococcal disease, especially in emerging countries (0-Brien et al. 2009 Lancet 374:893-902). The increasing number of antibiotic-resistant strains (Linares et al. 2010 Cin. Microbiol. Infect. 16:402-410) and the severity of pneumococcal diseases make vaccination the most effective intervention.

The major clinical syndromes caused by *S. pneumoniae* are widely recognized and discussed in all standard medical textbooks (Fedson D S, Muscher D M. In: Plotkin S A, Orenstein W A, editors. Vaccines. 4th edition. Philadelphia W B Saunders Co, 2004a: 529-588). For instance, Invasive pneumococcal disease (IPD) is defined as any infection in which *S. pneumoniae* is isolated from the blood or another normally sterile site (Musher D M. *Streptococcus pneumoniae*. In Mandell G L, Bennett J E, Dolin R (eds). Principles and Practice of Infectious diseases (5th ed). New York, Churchill Livingstone, 2001, p2128-2147). Chronic obstructive pulmonary disease (COPD) is recognised as encompassing several conditions (airflow obstruction, chronic bronchitis, bronchiolitis or small airways disease and emphysema) that often coexist (Wilson et al., Eur. Respir. J. 2001; 17: 995-1007). Patients suffer exacerbations of their condition that are usually associated with increased breathlessness, and often have increased cough that may be productive of mucus or purulent sputum (Wilson, Eur Respir J 2001 17:995-1007). COPD is defined physiologically by the presence of irreversible or partially reversible airway obstruction in patients with chronic bronchitis and/or emphysema (Standards for the diagnosis and care of patients with chronic obstructive pulmonary disease. American Thoracic Society. Am J Respir Crit Care Med. 1995 November; 152(5 Pt 2):S77-121). Exacerbations of COPD are often caused by bacterial (e.g. pneumococcal) infection (Sethi S, Murphy T F. Bacterial infection in chronic obstructive pulmonary disease in 2000: a state-of-the-art review. Clin Microbiol Rev. 2001 April; 14(2):336-63).

Pneumococcus is encapsulated with a chemically linked polysaccharide which confers serotype specificity. There are more than 90 known serotypes of pneumococci, and the capsule is the principle virulence determinant for pneumococci, as the capsule not only protects the inner surface of the bacteria from complement, but is itself poorly immunogenic. An anti-polysaccharide antibody level has been regarded as predictive of the protection against invasive pneumococcal disease (Jodar et al. Vaccine, (21) 2003, p. 3264-3272). After initial licensure of a 7-valent conjugate vaccine containing serotypes 4, 6B, 9V, 14, 18C, 19F, 23F (PCV7), two pneumococcal conjugate vaccines (PCVs) designed to broaden coverage have been licensed. The 10-valent pneumococcal *Haemophilus influenzae* protein D conjugate vaccine (PCV10) contains serotypes 1, 4, 5, 6B, 7F, 9V, 14 and 23F conjugated to nontypeable *H. influenzae* protein D, plus serotype 18C conjugated to tetanus toxoid and serotype 19F conjugated to diphtheria toxoid. The 13-valent pneumococcal conjugate vaccine (PCV13) contains the PCV7 (4, 6B, 9V, 14, 18C, 19F, 23F) serotypes plus serotypes 1, 3, 5, 6A, 7F and 19A, conjugated to cross-reactive material CRM197.

It is an object of the present invention to develop improved *Streptococcus pneumoniae* polysaccharides and improved *Streptococcus pneumoniae* polysaccharide conjugate vaccines.

*S. pneumoniae* serogroup 6 isolates, including isolates of serotypes 6A, 6B, 6C, and 6D, are important because they are commonly found in infections (Song et al. JOURNAL OF CLINICAL MICROBIOLOGY, May 2011, p. 1758-1764). WO2009/000826A2 discloses a *Streptococcus pneumoniae* serotype 6A capsular polysaccharide having a size 1100-1540 (Da×10³) conjugated to protein D and a *Streptococcus pneumoniae* serotype 6B capsular polysaccharide having a size 1069-1391 (Da×10³) conjugated to protein D (see Table 2 of WO2009/000826A2). Both the *Streptococcus pneumoniae* serotype 6A capsular polysaccharide and the *Streptococcus pneumoniae* serotype 6B capsular polysaccharide described in WO2009/000826A2 were native polysaccharides. The chemical structure of serotypes 6A and 6B only differs by the link between rhamnose and ribitol units. As the structure of polysaccharide 6A is very similar to polysaccharide 6B it was originally thought that a native PS6A (polysaccharide 6A) should be used for conjugation as a native PS6B (polysaccharide 6B) is used for conjugation. In the FinIP trial, PHiD-CV10 containing 6B conjugated to protein D was demonstrated to be effective against serotype 6B (Palmu et al. Lancet 2013; 381: 214-22). However, surprisingly, the present invention provides a sized *Streptococcus* 10 *pneumoniae* 6A polysaccharide with improved properties. The inventors have found that by using a *Streptococcus pneumoniae* serotype 6A capsular polysaccharide (PS6A) of a particular size, a conjugate may be obtained having both high immunogenicity and which is filterable.

DESCRIPTION OF THE INVENTION

Figure 1:
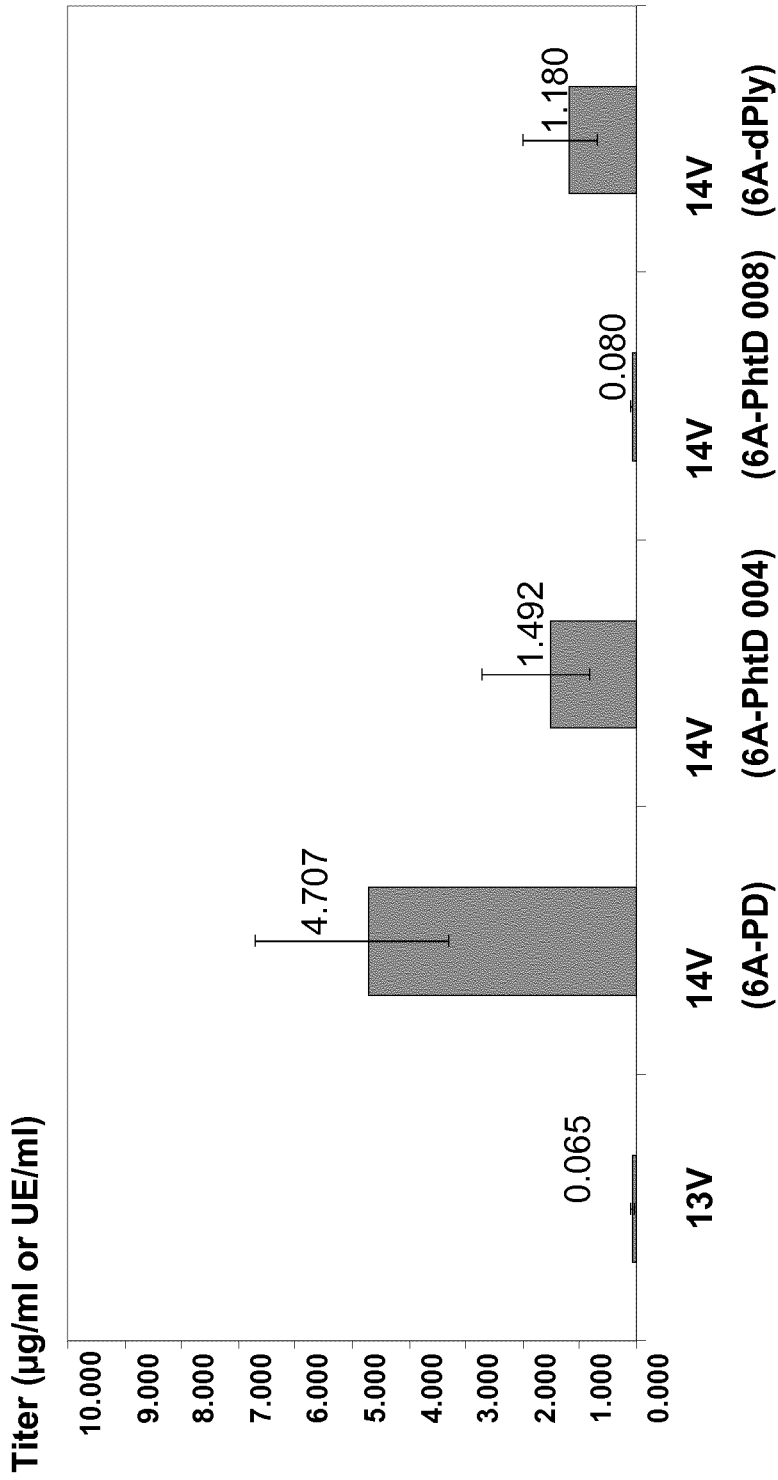
FIG. 1 Evaluation of PS6A conjugates in 14-valent (14V) AlPO4 formulation in the Balb/c mouse with co-administration of Infanrix™ Hexa model. ELISA anti-PS6A.

The present invention provides a sized *Streptococcus pneumoniae* serotype 6A capsular polysaccharide. In one aspect, the present invention provides a *Streptococcus pneumoniae* serotype 6A capsular polysaccharide wherein the average size ($M_w$) of the *S. pneumoniae* serotype 6A polysaccharide is between 100-1000, 110-750, 150-500, 180-600, 210-490, 210-450, 180-400, 210-400, 210-370, 220-360, 230-350, 240-340, 240-320, 240-310 or 250-310 kDa.

The term "polysaccharide" throughout this specification refers to a complex carbohydrate composed of a chain of saccharides joined together by glycosidic bonds. The polysaccharide may contain at least 2, 3, 4, 5, 6, 7, 8, 9, 10, 20, 30, 40 or 50 or more saccharides.

For the purposes of the invention, "native polysaccharide" refers to a polysaccharide that has not been subjected to a process (e.g. post-purification), the purpose of which is to reduce the size of the polysaccharide. A polysaccharide can become slightly reduced in size during normal purification procedures or by degradation during conjugation. Such a saccharide is still native. Only if the polysaccharide has been subjected to sizing techniques would the polysaccharide not be considered native.

For the purposes of the invention, "sized polysaccharide" refers to a polysaccharide that has been subjected to a process (e.g. post-purification), the purpose of which is to reduce the size of the polysaccharide. Polysaccharides may be sized by mechanical or chemical sizing techniques. Mechanical sizing techniques that may be used include high pressure techniques (such as microfluidization, Emulsiflex™, high pressure homogenization, or Gaulin homogenization) and sonication. Chemical sizing techniques that may be used include acid hydrolysis (e.g. treatment with acetic acid) or treatment with periodate. The term "periodate" includes both periodate and periodic acid; the term also includes both metaperiodate ($IO_4^-$) and orthoperiodate ($IO_6^{5-}$) and the various salts of periodate (e.g., sodium periodate and potassium periodate). The molecular weight ranges described herein refer to purified polysaccharides before conjugation (e.g. before activation where activation is carried out).

For the purposes of the invention, "sized by a factor up to ×2" means that the saccharide is subject to a process intended to reduce the size of the saccharide but to retain a size more than half the size of the native polysaccharide. Terms such as "sized by a factor up to" ×3, ×4 etc. are to be interpreted in the same way, i.e. the saccharide is subject to a process intended to reduce the size of the polysaccharide but to retain a size more than a third, a quarter etc., respectively, the size of the native polysaccharide.

The term "Molecular weight" or "average molecular weight" or "average size" of a polysaccharide as used herein refers to the weight-average molecular weight (MW) of the polysaccharide measured prior to conjugation measured by MALLS (Multi-Angle Laser Light Scattering).

The MALLS technique is known in the art and is typically carried out as described in below. For MALLS analysis of pneumococcal polysaccharides, two columns (TSKG6000 and 5000PWxl) may be used in combination and the polysaccharides are eluted in 0.2M NaCl. Polysaccharides are detected using a light scattering detector (for instance Wyatt Dawn DSP (Digital Signal Processing) equipped with a 10 mW argon laser at 488 nm) and an interferometric refractometer (for instance Wyatt Otilab DSP (Digital Signal Processing) equipped with a P100 cell and a red filter at 498 nm).

The laser light scattering detector measures the light intensities scattered at 16 angles by the macromolecular solution and on the other hand, an interferometric refractometer placed on-line allows the determination of the quantity of sample eluted. From these intensities, the size and shape of the macromolecules in solution can be determined.

The mean molecular weight in weight ($M_w$) is defined as the sum of the weights of all the species multiplied by their respective molecular weight and divided by the sum of weights of all the species.

a) Weight-average molecular weight: —$M_w$—

$$M_w = \frac{\sum W_i \cdot M_i}{\sum W_i} = \frac{m_2}{m_1}$$

b) Number-average molecular weight: —$M_n$—

$$M_n = \frac{\sum N_i \cdot M_i}{\sum N_i} = \frac{m_1}{m_0}$$

c) Root mean square radius: —$R_w$— and $r^2w$ is the square radius defined by:

$$R^2w \text{ or } (r^2)w = \frac{\sum m_i \cdot r_i^2}{\sum m_i}$$

(—$m_i$— is the mass of a scattering centre i and —$r_i$— is the distance between the scattering centre i and the center of gravity of the macromolecule).

d) The polydispersity is defined as the ratio —$M_w/M_n$—.

As used herein, the term "treatment" (including variations thereof, e.g. "treat" or "treated") means any one or more of the following: (i) the prevention of infection or re-infection, as in a traditional vaccine, (ii) the reduction in the severity of, or, in the elimination of symptoms, (iii) the delay in recurrence of symptoms, and (iii) the substantial or complete elimination of the pathogen or disorder in question in a subject. Hence, treatment may be effected prophylactically (prior to infection) or therapeutically (following infection).

For the purposes of this invention, "treatment or prevention of exacerbations of COPD" or "reduction in severity of COPD exacerbations" refers to a reduction in incidence or rate of COPD exacerbations (for instance a reduction in rate of 0.1, 0.5, 1, 2, 5, 10, 20% or more) or a reduction in severity of COPD exacerbations (e.g. airflow obstruction, chronic bronchitis, bronchiolitis or small airways disease and emphysema), for instance within a patient group immunized with the immunogenic compositions or vaccines of the invention.

Sized *Streptococcus pneumoniae* Serotype 6A Capsular Polysaccharides

*Streptococcus pneumoniae* serotype 6A capsular polysaccharides may be sized by mechanical or chemical sizing techniques. In an embodiment, the *Streptococcus pneumoniae* serotype 6A capsular polysaccharides of the invention are sized by a chemical sizing technique. Chemical sizing techniques that may be used include treatment with acetic acid or treatment with periodate. In one aspect, the *Streptococcus pneumoniae* serotype 6A capsular polysaccharides of the invention are sized by treatment with periodate. The term "periodate" includes both periodate and periodic acid; the term also includes both metaperiodate ($IO_4^-$) and orthoperiodate ($IO_6^{5-}$) and the various salts of periodate (e.g., sodium periodate and potassium periodate). In another aspect, the *Streptococcus pneumoniae* serotype 6A capsular polysaccharides of the invention are sized by treatment with acetic acid. In an embodiment, the *Streptococcus pneumoniae* serotype 6A capsular polysaccharides of the invention are sized by a mechanical sizing technique, for example using a high pressure technique. High pressure techniques include microfluidization, high pressure homogenization, or Gaulin homogenization. In one aspect, the *Streptococcus pneumoniae* serotype 6A capsular polysaccharide of the invention is sized by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer. The technique of high pressure homogenization is described in Cho et al. (*Int. J. Mol. Sci.* 2014, 15). In another aspect of the invention, the *Streptococcus pneumoniae* serotype 6A capsular polysaccharide of the invention is sized by Gaulin homogenization. Gaulin homogenization may be carried out using the technique described in Lander et al. (*Biotechnol. Prog.* 2000, 16, 80-85). In another aspect, the *Streptococcus pneumoniae* serotype 6A capsular polysaccharide of the invention is sized by microfluidization (for example as described in the Examples below).

Sized *Streptococcus pneumoniae* serotype 6A capsular polysaccharides of the present invention have an average size ($M_w$) between 100-1000, 110-750, 150-500, 180-600, 210-490, 210-450, 180-400, 210-400, 210-370, 220-360, 230-350, 240-340, 240-320, 240-310 or 250-310 kDa. Sizing is by a factor of no more than ×20, ×10, ×8, ×6, ×5, ×4, ×3 or ×2. For example, sizing may be from a factor of between ×2 to ×6, ×2 to ×5, ×2 to ×4, or ×3 to ×6, ×3 to ×5 or ×3 to ×4. In one aspect, the *Streptococcus pneumoniae* serotype 6A capsular polysaccharide of the invention is sized by a factor of no more than ×5. The molecular weight ranges described herein refer to molecular weight of the purified *Streptococcus pneumoniae* serotype 6A capsular polysaccharides before conjugation (e.g., before activation where activation is carried out).

In an embodiment, the sized *Streptococcus pneumoniae* serotype 6A capsular polysaccharide of the invention is antigenic (as determined by ELISA), for example having an antigenicity index of between 70 to 200%, preferably between 90% and 150% (e.g. between 120 and 144%). As explained in the Examples below, the antigenicity index is measured relative to native *Streptococcus pneumoniae* serotype 6A capsular polysaccharide which is assigned an antigenicity index of 100% (also represented as 1.0 in the tables below).

Conjugated *Streptococcus pneumoniae* Serotype 6A Capsular Polysaccharides

Suitably, the sized *Streptococcus pneumoniae* serotype 6A capsular polysaccharide of the invention is conjugated to a carrier protein. The carrier protein may be selected from the group consisting of TT (tetanus toxoid), DT (diphtheria toxoid), CRM197, fragment C of TT, PhtD (pneumococcal histidine triad protein D), PhtDE fusions (a fusion of PhtD and PhtE (pneumococcal histidine protein E) particularly those described in WO 01/98334 and WO 03/54007), detoxified pneumolysin and protein D. In one aspect of the invention, the sized *Streptococcus pneumoniae* serotype 6A capsular polysaccharide is conjugated to a carrier protein selected from the group consisting of TT (tetanus toxoid), DT (diphtheria toxoid), CRM197, fragment C of TT, and PhtD (pneumococcal histidine triad protein D). In another aspect of the invention, the sized *Streptococcus pneumoniae* serotype 6A capsular polysaccharide of the invention is conjugated DT or CRM197. In another aspect of the invention, the sized *Streptococcus pneumoniae* serotype 6A capsular polysaccharide of the invention is conjugated to CRM197.

CRM197 is a non-toxic form of the diphtheria toxin but is immunologically indistinguishable from the diphtheria toxin (DT). Genetically detoxified analogues of diphtheria toxin include CRM197 and other mutants described in U.S. Pat. Nos. 4,709,017, 5,843,711, 5,601,827, and U.S. Pat. No. 5,917,017. CRM197 is produced by *C. diphtheriae* infected by the nontoxigenic phase β197tox-created by nitrosoguanidine mutagenesis of the toxigenic carynephage b (Uchida et al Nature New Biology (1971) 233; 8-11). The CRM197 protein has the same molecular weight as the diphtheria toxin but differs from it by a single base change in the structural gene. This leads to a glycine to glutamine change of amino acid at position 52 which makes fragment A unable to bind NAD and therefore non-toxic (Pappenheimer 1977, Ann Rev, Biochem. 46; 69-94, Rappuoli Applied and Environmental Microbiology Sept 1983 p560-564).

Fragment C of TT is the non-toxic carboxy-terminal fragment of the tetanus toxin heavy chain. Tetanus toxin is a single peptide of approximately 150 kDa, which consists of 1315 amino-acid residues. Cleavage of tetanus-toxin by papain yields two fragments; one of them, fragment C, is approximately 50 kDa. Fragment C of TT is further described in Neubauer et al. *Biochim. Biophys. Acta* 1981, 27, 141-148.

In an embodiment, the sized *Streptococcus pneumoniae* serotype 6A capsular polysaccharide of the invention is conjugated to the carrier protein via a linker, for instance a bifunctional linker (having two reactive ends). The linker is optionally heterobifunctional (having different reactive groups at either end) or homobifunctional (having identical reactive groups at either end of a spacer arm), for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH (adipic acid dihydrazide). Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. Nos. 4,673,574, 4,808,700), hexane diamine and 6-aminocaproic acid (U.S. Pat. No. 4,459,286). In another embodiment, the sized *Streptococcus pneumoniae* serotype 6A capsular polysaccharide of the invention is directly conjugated to the carrier protein. In one aspect, the sized *Streptococcus pneumoniae* serotype 6A capsular polysaccharide of the invention is linked to carrier protein via an isourea link. An isourea link is formed by the reaction between a cyanate ester on polysaccharide and an amino group on the carrier. Reference to an "isourea link" herein refers to a stable link.

Immunogenic Compositions

In an embodiment, the present invention provides an immunogenic composition comprising a sized *Streptococcus pneumoniae* serotype 6A capsular polysaccharide (or conjugate) of the invention.

Typically the immunogenic compositions of the invention will comprise capsular polysaccharide antigens (suitably conjugated), wherein the polysaccharides are derived from at least ten serotypes of *S. pneumoniae*. The number of *S. pneumoniae* capsular polysaccharides can range from 10 different serotypes (or valences "v") to 23 different serotypes (23v, a 23 valent composition). In one embodiment the immunogenic composition comprises 10 or more, 11 or more, 12 or more, 13 or more, 14 or more, 15 or more or 15 or more capsular polysaccharides from different *S. pneumoniae* serotypes. In one embodiment, there are 10, 11, 12, 13, 14 or 15 different *S. pneumoniae* serotypes. In another embodiment, the immunogenic composition of the invention may comprise conjugated *S. pneumoniae* polysaccharides and unconjugated *S. pneumoniae* polysaccharides. In an embodiment, the total number of saccharide serotypes is less than or equal to 23.

In one embodiment the multivalent pneumococcal vaccine of the invention will comprise polysaccharides (suitably conjugated) selected from the following serotypes 1, 2, 3, 4, 5, 6A, 6B, 7F, 8, 9N, 9V, 10A, 11A, 12F, 14, 15B, 15C, 17F, 18C, 19A, 19F, 20, 22F, 23F and 33F, although it is appreciated that one or two other serotypes could be substituted depending on the age of the recipient receiving the vaccine and the geographical location where the vaccine will be administered. In an embodiment, the vaccine may be an 11-valent vaccine. For example, a 11-valent vaccine may comprise polysaccharides from serotypes 1, 4, 5, 6A, 6B, 7F, 9V, 14, 18C, 19F and 23F. In an embodiment, the vaccine may be an 12-valent or 13-valent vaccine. A 12 or 13-valent paediatric (infant) vaccine may also include the 11 valent formulation supplemented with serotypes 19A, or 22F, or 15, or 19A and 22F, or 19A and 15, or 22F and 15, whereas a 13-valent elderly vaccine may include the 11 valent formulation supplemented with serotypes 19A and 22F, 8 and 12F, or 8 and 15, or 8 and 19A, or 8 and 22F, or 12F and 15, or 12F and 19A, or 12F and 22F, or 15 and 19A, or 15 and 22F. In an embodiment, the vaccine may be a 14-valent or 15-valent vaccine. A 14 or 15-valent paediatric vaccine may include the 11 valent formulation described above supplemented with serotypes 3, 19A and 22F; serotypes 8, 19A and 22F; serotypes 12F, 19A and 22F; serotypes 15, 19A and 22F; serotypes 3, 8, 19A and 22F; serotypes 3, 12F, 19A and 22F; serotypes 3, 15, 19A and 22F. In an embodiment, the vaccine may be a 16-valent vaccine. A 16 valent vaccine may include the 11 valent formulation described above supplemented with serotypes 3, 15B, 19A, 22F and 23F. A 16 valent vaccine may include the 11 valent formulation described above supplemented with serotypes 3, 15B, 19A, 22F and 33F. In an embodiment, the vaccine may be a 19-valent vaccine. A 19 valent vaccine may include the 11 valent formulation described above supplemented with serotypes 8, 10A, 11A, 12F, 15B, 19A, 22F and 23F. A 19 valent vaccine may include the 11 valent formulation described above supplemented with serotypes 8, 10A, 11A, 12F, 15B, 19A, 22F and 33F. In an embodiment, the vaccine may be a 20-valent vaccine. A 20 valent vaccine may include the 11 valent formulation described above supplemented with serotypes 3, 8, 10A, 11A, 12F, 15B, 19A, 22F and 23F. A 20 valent vaccine may include the 11 valent formulation described above supplemented with serotypes 3, 8, 10A, 11A, 12F, 15B, 19A, 22F and 33F. In an embodiment, the vaccine may be a 21-valent vaccine.

In one embodiment, the immunogenic composition of the invention comprises capsular polysaccharides derived from serotypes 1, 4, 5, 6A, 6B, 7F, 9V, 14, 18C, 19F and 23F (suitably conjugated). In a further embodiment of the invention at least 12 saccharide antigens (suitably conjugated) are included, for example capsular polysaccharides derived from serotypes 1, 4, 5, 6A, 6B, 7F, 9V, 14, 18C, 19A, 19F and 23F. In a further embodiment of the invention at least 12 saccharide antigens (suitably conjugated) are included, for example capsular polysaccharides derived from serotypes 1, 3, 4, 5, 6A, 6B, 7F, 9V, 14, 18C, 19F and 23F. In a further embodiment of the invention, at least 13 polysaccharide antigens (suitably conjugated) are included, for example a vaccine may comprise capsular polysaccharides derived from serotypes 1, 3, 4, 5, 6A, 6B, 7F, 9V, 14, 18C, 19A, 19F and 23F, although further saccharide antigens, for example 23 valents (such as serotypes 1, 2, 3, 4, 5, 6B, 7F, 8, 9N, 9V, 10A, 11A, 12F, 14, 15, 17F, 18C, 19A, 19F, 20, 22F, 23F and 33F), are also contemplated by the invention. In a further embodiment of the invention, at least 15 saccharide antigens (suitably conjugated) are included, for example capsular polysaccharides derived from serotypes 1, 3, 4, 5, 6A, 6B, 7F, 9V, 14, 18C, 19A, 19F, 22F, 23F and 33F. In a further embodiment of the invention, at least 15 saccharide antigens (suitably conjugated) are included, for example capsular polysaccharides derived from serotypes 1, 4, 5, 6A, 6B, 7F, 9V, 14, 15B, 18C, 19A, 19F 22F, 23F and 33F. In a further embodiment of the invention, at least 16 saccharide antigens (suitably conjugated) are included, for example capsular polysaccharides derived from serotypes 1, 3, 4, 5, 6A, 6B, 7F, 9V, 14, 15B, 18C, 19A, 19F 22F, 23F and 33F. In another embodiment, the immunogenic composition comprises (conjugated) capsular (poly)saccharide of serotype 33F of *S. pneumoniae*. In another embodiment, the immunogenic composition comprises (conjugated) capsular (poly)saccharide of serotype 15C of *S. pneumoniae*. In another embodiment, the immunogenic composition comprises (conjugated) capsular (poly)saccharide of serotype 12F of *S. pneumoniae*. In an embodiment, there are 10 to 23 different *S. pneumoniae* capsular polysaccharide serotypes (suitably conjugated).

Carrier Proteins

Examples of carrier proteins which may be used in the present invention are DT (Diphtheria toxoid), TT (tetanus toxoid) or fragment C of TT, DT, CRM197 other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709, 017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment of DT disclosed in U.S. Pat. No. 5,843,711, pneumococcal pneumolysin (Kuo et al (1995) Infect Immun 63; 2706-13) including pneumolysin (Ply) detoxified in some fashion for example GMBS detoxified pneumolysin (dPly-GMBS) (WO 04081515, PCT/EP2005/010258) or formaldehyde detoxified pneumolysin (dPly-formol), Pht (pneumococcal histidine triad) family proteins (PhtX), including PhtA, PhtB, PhtD, PhtE and fusions of Pht proteins for example PhtDE fusions, PhtBE fusions (WO 01/98334 and WO 03/54007), (Pht A-E are described in more detail below) OMPC (meningococcal outer membrane protein—usually extracted from *N. meningitidis* serogroup B—EP0372501), *Neisseria meningitidis* porin PorB, PD (*Haemophilus influenzae* protein D—see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *Clostridium difficile* (WO 00/61761).

In an embodiment, in the immunogenic composition of the invention each *Streptococcus pneumoniae* capsular saccharide is conjugated to a carrier protein independently selected from the group consisting of DT, CRM 197, TT, Fragment C of TT, dPly (detoxified pneumolysin), PhtA, PhtB, PhtD, PhtE, PhtDE OmpC, PorB and *Haemophilus influenzae* Protein D. In a further embodiment, each *Streptococcus pneumoniae* capsular saccharide is conjugated to a carrier protein independently selected from the group consisting of TT, DT, CRM197, fragment C of TT, PhtD, PhtDE fusions (particularly those described in WO 01/98334 and WO 03/54007), detoxified pneumolysin and protein D. In a further embodiment, each *Streptococcus pneumoniae* capsular saccharide is conjugated to a carrier protein independently selected from the group consisting of TT, DT, CRM197, PhtD, detoxified pneumolysin and protein D. In a further embodiment, each *Streptococcus pneumoniae* capsular saccharide is conjugated to a carrier protein independently selected from the group consisting of TT, DT, CRM197, PhtD and protein D. In a further embodiment, each *Streptococcus pneumoniae* capsular saccharide is conjugated to a carrier protein independently selected from the group consisting of TT, DT, CRM197 and protein D.

In an embodiment, the immunogenic composition of the invention comprises two or more different carrier proteins. In an embodiment, the immunogenic composition of the invention comprises 2, 3, 4, 5 or 6 different carrier proteins. Each type of carrier protein may act as carrier for more than one polysaccharide, which polysaccharides may be from the same or different serotypes. In one embodiment, two or more different polysaccharide serotypes may be conjugated to the same carrier protein, either to the same molecule of carrier protein (carrier molecules having 2 or more different polysaccharide serotypes conjugated to it) [see for instance WO 04/083251] or to different molecules of the same carrier protein (each molecule of protein carrier only having one serotype of saccharide conjugated to it).

In an embodiment, the immunogenic composition of the invention comprises protein D from *Haemophilus influenzae* (PD), for example, protein D sequence from FIG. 9 (FIGS. 9a and 9b together, 364 amino acids) of EP 0594610 (SEQ ID NO: 1). Inclusion of this protein in the immunogenic composition may provide a level of protection against *Haemophilus influenzae* related otitis media (Pyrmula et al Lancet 367; 740-748 (2006)). Protein D may be used as a full length protein or as a fragment (for example, Protein D may be as described in WO0056360). For example, a protein D sequence may comprise (or consist) of the protein D fragment described in EP0594610 which begins at the sequence SSHSSNMANT (SerSerHisSerSerAsnMetAlaAsnThr) (SEQ ID NO: 3), and lacks the 19 N-terminal amino acids from FIG. 9 of EP0594610, optionally with the tripeptide MDP from NS1 fused to the N-terminal of said protein D fragment (348 amino acids) (SEQ ID NO: 2). In one aspect, the protein D or fragment of protein D is unlipidated. The protein D could be present in the immunogenic composition as a free protein or as a carrier protein. In one aspect, protein D is present in the immunogenic composition as free protein. In another aspect, protein D is present both as a carrier protein and as free protein. In a further aspect, protein D is present as a carrier protein for one or more of the polysaccharides. In a further aspect, 2-9 of the capsular polysaccharides selected from different serotypes are conjugated to protein D. In a further aspect, protein D is present as a carrier protein for the majority of the polysaccharides, for example 6, 7, 8, 9 or more of the polysaccharides may be conjugated to protein D.

In an embodiment, the immunogenic composition of the invention contains 2-8, 2-7, 2-6, 2-5, 3-5, 4-5, 2-4, 2-3, 3-4 or 2, 3, 4, 5, 6, 7 or 8 capsular saccharide serotype conjugates in which protein D is the carrier protein. For example, 2-8, 2-7, 2-6, 2-5, 3-5, 4-5, 2-4, 2-3, 3-4 or 2, 3, 4, 5, 6, 7 or 8 polysaccharides selected from serotype 1, 3, 4, 5, 6B, 7F, 9V, 14, 18C, 19A, 19F, 22F and 23F are conjugated to protein D. For example, polysaccharides from serotypes 1, 4, 5, 6B, 7F, 9V, 14 and 23F are conjugated to protein D.

In an embodiment, polysaccharides from at least serotypes 1 and 3, 1 and 4, 1 and 5, 1 and 6A, 1 and 6B, 1 and 7, 1 and 9V, 1 and 14, 1 and 22F, 1 and 23F, 3 and 4, 3 and 5, 3 and 6A, 3 and 6B, 3 and 7F, 3 and 9V, 3 and 14, 3 and 22F, 3 and 23F, 4 and 5, 4 and 6A, 4 and 6B, 4 and 7F, 4 and 9V, 4 and 14, 4 and 22F, 4 and 23F, 5 and 6A, 5 and 6B, 5 and 7F, 5 and 9V, 5 and 14, 5 and 22F, 5 and 23F, 6A and 6B, 6A and 7F, 6A and 9V, 6A and 14, 6A and 22F, 6A and 23F, 6B and 7F, 6B and 9V, 6B and 14, 6B and 22F, 6B and 23F, 7F and 9V, 7F and 14, 7F and 22F, 7F and 23F, 9V and 14, 9V and 22F, 9V and 23F, 14 and 22F, 14 and 23F or 22F and 23F are conjugated to protein D.

In an embodiment, polysaccharides from at least serotypes 1, 3 and 4; 1, 3 and 5; 1, 3 and 6A; 1, 3 and 6B; 1, 3 and 7F; 1, 3 and 9V; 1, 3 and 14; 3, 4 and 7F; 3, 4 and 5; 3, 4 and 7F; 3, 4 and 9V; 3, 4 and 14; 4, 5 and 7F; 4, 5 and 9V; 4, 5, and 14; 5, 7F and 9V; 5, 7F and 14; 7F, 9V and 14; 1, 3, 4 and 5; 3, 4, 5 and 7F; 4, 5, 7F and 9V; 4, 5, 7F and 14; 4, 5, 9V and 14; 4, 7F, 9V and 14; 5, 7F, 9V and 14; or 4, 5, 7F, 9V and 14 are conjugated to protein D.

For example, in a 10 valent *S. pneumoniae* immunogenic composition, 2, 3, 4, 5, 6, 7 or 8 of the capsular polysaccharides from different serotypes are conjugated to protein D. For example, in a 11 valent *S. pneumoniae* immunogenic composition, 2, 3, 4, 5, 6, 7 or 8 of the capsular polysaccharides from different serotypes are conjugated to protein D. For example, in a 12 valent *S. pneumoniae* immunogenic composition, 2, 3, 4, 5, 6, 7 or 8 of the capsular polysaccharides from different serotypes are conjugated to protein D. For example, in a 13 valent *S. pneumoniae* immunogenic composition, 2, 3, 4, 5, 6, 7 or 8 of the capsular polysaccharides from different serotypes are conjugated to protein D. For example, in a 14 valent *S. pneumoniae* immunogenic composition, 2, 3, 4, 5, 6, 7 or 8 of the capsular polysaccharides from different serotypes are conjugated to protein D. For example, in a 15 valent *S. pneumoniae* immunogenic composition, 2, 3, 4, 5, 6, 7 or 8 of the capsular polysaccharides from different serotypes are conjugated to protein D. For example, in a 16 valent *S. pneumoniae* immunogenic composition, 2, 3, 4, 5, 6, 7 or 8 of the capsular polysaccharides from different serotypes are conjugated to protein D. For example, in a 17 valent *S. pneumoniae* immunogenic composition, 2, 3, 4, 5, 6, 7 or 8 of the capsular polysaccharides from different serotypes are conjugated to protein D. For example, in a 18 valent *S. pneumoniae* immunogenic composition, 2, 3, 4, 5, 6, 7, 8 or 9 of the capsular polysaccharides from different serotypes are conjugated to protein D. For example, in a 19 valent *S. pneumoniae* immunogenic composition, 2, 3, 4, 5, 6, 7, 8 or 9 of the capsular polysaccharides from different serotypes are conjugated to protein D. Optionally, the serotypes conjugated to protein D are selected from the groups described above.

In an embodiment, the immunogenic composition of the invention comprises at least one capsular saccharide conjugated to tetanus toxoid (TT). In another embodiment, capsular saccharide 18C is conjugated to TT, optionally wherein 18C is the only saccharide in the composition conjugated to tetanus toxoid (TT).

In an aspect of the present invention, serotype 19F is conjugated to DT or CRM197. In another aspect, serotype 19F is conjugated to DT. In one aspect, the remaining saccharide serotypes of the immunogenic composition may all be conjugated to one or more carrier proteins that are not DT (i.e. only 19F is conjugated to DT). In one embodiment, 19F is conjugated to DT or CRM197, and the remaining serotypes are conjugated to carrier proteins independently selected from PhtD, PD (Protein D), TT (Tetanus Toxoid), DT (Diphtheria Toxoid) and CRM197. In another embodiment, 19F is conjugated to DT or CRM 197, and the remaining serotypes are conjugated to carrier proteins independently selected from PD, TT, DT and CRM197. In a further embodiment, 19F is conjugated to DT or CRM 197, and the remaining serotypes are conjugated to carrier proteins independently selected from PD, TT and CRM197 (for example as described in WO2007/071710A2 and WO2007/071707A2).

In an embodiment, the sized *Streptococcus pneumoniae* serotype 6A capsular polysaccharide of the invention and *Streptococcus pneumoniae* serotype 6B capsular polysaccharide are conjugated to different carrier proteins. In a further embodiment, the sized *Streptococcus pneumoniae* serotype 6A capsular polysaccharide of the invention is conjugated to CRM 197. In a further embodiment a *Streptococcus pneumoniae* serotype 6B capsular polysaccharide conjugate is present, but is not conjugated to DT or CRM 197. In a further embodiment, the sized *Streptococcus pneumoniae* serotype 6A capsular polysaccharide is conjugated to CRM197 and *Streptococcus pneumoniae* serotype 6B capsular polysaccharide *Streptococcus pneumoniae* serotype is conjugated to a carrier protein other than CRM197. In a further embodiment, the sized *Streptococcus pneumoniae* serotype 6A capsular polysaccharide is conjugated to CRM197 and *Streptococcus pneumoniae* serotype 6B capsular polysaccharide *Streptococcus pneumoniae* serotype is conjugated to a carrier protein selected from PhtD, PD (Protein D), TT (Tetanus Toxoid) or DT (Diphtheria Toxoid). In a further embodiment, the sized *Streptococcus pneumoniae* serotype 6A capsular polysaccharide is conjugated to CRM197 and *Streptococcus pneumoniae* serotype 6B capsular polysaccharide is conjugated to protein D.

In an embodiment of the invention, the carrier protein conjugated to one or more of the *S. pneumoniae* capsular polysaccharides is a member of the polyhistidine triad family (Pht) proteins, fragments or fusion proteins thereof. The PhtA, PhtB, PhtD or PhtE proteins may have an amino acid sequence sharing 80%, 85%, 90%, 95%, 98%, 99% or 100% identity with a sequence disclosed in WO 00/37105 or WO 00/39299 (e.g. with amino acid sequence 1-838 or 21-838 of SEQ ID NO: 4 of WO 00/37105 for PhtD). For example, fusion proteins are composed of full length or fragments of 2, 3 or 4 of PhtA, PhtB, PhtD, PhtE. Examples of fusion proteins are PhtA/B, PhtA/D, PhtA/E, PhtB/A, PhtB/D, PhtB/E. PhtD/A. PhtD/B, PhtD/E, PhtE/A, PhtE/B and PhtE/D, wherein the proteins are linked with the first mentioned at the N-terminus (see for example WO01/98334).

Where fragments of Pht proteins are used (separately or as part of a fusion protein), each fragment optionally contains one or more histidine triad motif(s) and/or coiled coil regions of such polypeptides. A histidine triad motif is the portion of polypeptide that has the sequence HxxHxH where H is histidine and x is an amino acid other than histidine. A coiled coil region is a region predicted by "Coils" algorithm Lupus, A et al (1991) Science 252; 1162-1164. In an embodiment, the fragment includes one or more histidine triad motif as well as at least one coiled coil region. In an embodiment, the fragment contains exactly or at least 2, 3, 4 or 5 histidine triad motifs (optionally, with native Pht sequence between the 2 or more triads, or intra-triad sequence that is more than 50, 60, 70, 80, 90 or 100% identical to a native pneumococcal intra-triad Pht sequence—e.g. the intra-triad sequence shown in SEQ ID NO: 4 of WO 00/37105 for PhtD). In an embodiment, the fragment contains exactly or at least 2, 3 or 4 coiled coil regions. In an embodiment, a Pht protein disclosed herein includes the full length protein with the signal sequence attached, the mature full length protein with the signal peptide (for example 20 amino acids at N-terminus) removed, naturally occurring variants of Pht protein and immunogenic fragments of Pht protein (e.g. fragments as described above or polypeptides comprising at least 15 or 20 contiguous amino acids from an amino acid sequence in WO00/37105 (SEQ ID NOs 4, 6, 8 or 10) or WO00/39299 (SEQ ID NOs 2, 4, 6, 8, 10 or 14) wherein said polypeptide is capable of eliciting an immune response specific for said amino acid sequence in WO00/37105 or WO00/39299).

In particular, the term "PhtD" as used herein includes the full length protein with the signal sequence attached, the mature full length protein with the signal peptide (for example 20 amino acids at N-terminus) removed, naturally occurring variants of PhtD and immunogenic fragments of PhtD (e.g. fragments as described above or polypeptides comprising at least or 20 contiguous amino acids from a PhtD amino acid sequence in WO00/37105 or WO00/39299) wherein said polypeptide is capable of eliciting an immune response specific for said PhtD amino acid sequence in WO00/37105 or WO00/39299 (e.g. SEQ ID NO: 4 of WO 00/37105 or SEQ ID NO: 14 of WO 00/39299 for PhtD). All forms of PhtD mentioned above can be used in the present invention.

Conjugation Processes

The saccharide conjugates present in the immunogenic compositions of the invention may be prepared by the conjugation methods of the present invention or any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS (4-Maleimidobutyric acid N-hydroxysuccinimide ester)) or a haloacetylated carrier protein (for example using SIAB (succinimidyl (4-iodoacetyl)aminobenzoate), or SIA (succinimidyl iodoacetate), or SBAP (succinimidyl-3-(bromoacetamide)propionate)). In an embodiment, the cyanate ester (optionally made by CDAP chemistry) is coupled with hexane diamine or ADH (adipic acid dihydrazide) and the amino-derivatised saccharide is conjugated to the carrier protein using carbodiimide (e.g. 1-Ethyl-3-(3-dimethylaminopropyl)carbodiimide (EDAC or EDC)) chemistry via a carboxyl group on the protein carrier. Such conjugates are described in PCT published application WO 93/15760 Uniformed Services University and WO 95/08348 and WO 96/29094.

In an embodiment, at least one of the S. pneumoniae capsular polysaccharides is directly conjugated to a carrier protein (e.g. using one of the chemistries described above). In an embodiment, at least one of the S. pneumoniae capsular polysaccharides is directly conjugated by 1-cyano-4-dimethylaminopyridinium tetrafluoroborate (CDAP). In an embodiment, the majority of the capsular polysaccharides for example 5, 6, 7, 8, 9 or more are directly linked to the carrier protein by CDAP (see WO 95/08348 and WO 96/29094)

In an embodiment, the Streptococcus pneumoniae polysaccharide is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH (adipic acid dihydrazide). Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. No. 4,673,574, 4,808,700), hexane diamine and 6-aminocaproic acid (U.S. Pat. No. 4,459,286). In an embodiment, the immunogenic composition of the invention may comprise 18C capsular polysaccharide conjugated to the carrier protein via a linker, optionally the linker is ADH. In an embodiment, the immunogenic composition of the invention may comprise 22F capsular polysaccharide conjugated to the carrier protein via a linker, optionally the linker is ADH (for example as described in WO2007/071711A2).

Other suitable techniques use carbodiimides, hydrazides, active esters, norborane, p-nitrobenzoic acid, N-hydroxysuccinimide, N-hydroxysulfosuccinimide (S—NHS), EDC, 0-(N-Succinimidyl)-1,1,3,3-tetramethyl-uronium tetrafluoroborate (TSTU). Many are described in WO 98/42721. Conjugation may involve a carbonyl linker which may be formed by reaction of a free hydroxyl group of the polysaccharide with Carbonyldiimidazole (CDI) (Bethell et al J. Biol. Chem. 1979, 254; 2572-4, Hearn et al J. Chromatogr. 1981.218; 509-18) followed by reaction of with a protein to form a carbamate linkage. This may involve reduction of the anomeric terminus to a primary hydroxyl group, optional protection/deprotection of the primary hydroxyl group reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated polysaccharide derivatised with adipic acid dihydrazide (ADH) to the protein carrier by Carbodiimide condensation (Chu C. et al Infect. Immunity, 1983 245 256), for example using EDAC.

In an embodiment, at least one S. pneumoniae polysaccharide is conjugated to a carrier protein via a linker using CDAP and EDAC. For example, 18C or 22F may be conjugated to a protein via a linker (for example those with two hydrazino groups at its ends such as ADH) using CDAP and EDAC as described above. When a linker is used, CDAP may be used to conjugate the polysaccharide to a linker and EDAC may then be used to conjugate the linker to a protein or, alternatively EDAC may be used first to conjugate the linker to the protein, after which CDAP may be used to conjugate the linker to the saccharide.

In an embodiment, a hydroxyl group (suitably an activated hydroxyl group for example a hydroxyl group activated to make a cyanate ester [e.g. with CDAP]) on a polysaccharide is linked to an amino or carboxylic group on a protein either directly or indirectly (through a linker). Where a linker is present, a hydroxyl group on a polysaccharide is suitably linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the pneumococcal capsular saccharide(s) is conjugated to the linker first before the linker is conjugated to the carrier protein. Alternatively the linker may be conjugated to the carrier before conjugation to the saccharide.

A combination of techniques may also be used, with some saccharide-protein conjugates being prepared by CDAP, and some by reductive amination.

In general the following types of chemical groups on a protein carrier can be used for coupling/conjugation:

A) Carboxyl (for instance via aspartic acid or glutamic acid). In one embodiment this group is linked to amino groups on polysaccharides directly or to an amino group on a linker with carbodiimide chemistry e.g. with EDAC.

B) Amino group (for instance via lysine). In one embodiment this group is linked to carboxyl groups on polysaccharides directly or to a carboxyl group on a linker with carbodiimide chemistry e.g. with EDAC. In another embodiment this group is linked to hydroxyl groups activated with CDAP or CNBr on polysaccharides directly or to such groups on a linker; to polysaccharides or linkers having an aldehyde group; to polysaccharides or linkers having a succinimide ester group.

C) Sulphydryl (for instance via cysteine). In one embodiment this group is linked to a bromo or chloro acetylated polysaccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or $NH_2$. Aldehyde groups can be generated after different treatments known in the art such as: periodate, acid hydrolysis, hydrogen peroxide, etc.

Direct Coupling Approaches:

Saccharide-OH+CNBr or CDAP→cyanate ester+$NH_2$-Protein→conjugate

Saccharide-aldehyde+$NH_2$-Protein→Schiff base+NaCNBH3→conjugate

Saccharide-COOH+$NH_2$-Protein+EDAC→conjugate

Saccharide-$NH_2$+COOH-Protein+EDAC→conjugate

Indirect Coupling Via Spacer (Linker) Approaches:

Saccharide-OH+CNBr or CDAP→cyanate ester+$NH_2$—$NH_2$→saccharide-$NH_2$+COOH-Protein+EDAC→conjugate Saccharide-OH+CNBr or CDAP→cyanate ester+$NH_2$—SH→saccharide-SH+SH-Protein (native Protein with an exposed cysteine or obtained after modification of amino groups of the protein by SPDP for instance)→saccharide-S—S-Protein Saccharide-OH+CNBr or CDAP→cyanate ester+$NH_2$—SH→saccharide-SH+maleimide-Protein (modification of amino groups)→conjugate Saccharide-OH+CNBr or CDAP→cyanate ester+$NH_2$—SH→Saccharide-SH+haloacetylated-Protein→Conjugate Saccharide-COOH+EDAC+$NH_2$—$NH_2$→saccharide $NH_2$+EDAC+COOH-Protein→conjugate Saccharide-COOH+EDAC+$NH_2$—SH→saccharide-SH+SH-Protein (native Protein with an exposed cysteine or obtained after modification of amino groups of the protein by SPDP for instance)→saccharide-S—S-Protein Saccharide-COOH+EDAC+$NH_2$—SH→saccharide-SH+maleimide-Protein (modification of amino groups)→conjugate Saccharide-COOH+EDAC+$NH_2$—SH→Saccharide-SH+haloacetylated-Protein→Conjugate Saccharide-Aldehyde+$NH_2$—$NH_2$→saccharide-$NH_2$+EDAC+COOH-Protein→conjugate Note: instead of EDAC above, any suitable carbodiimide may be used.

In summary, the types of protein carrier chemical group that may be generally used for coupling with a polysaccharide are amino groups (for instance on lysine residues), COOH groups (for instance on aspartic and glutamic acid residues) and SH groups (if accessible) (for instance on cysteine residues).

In an embodiment, the *Streptococcus pneumoniae* serotype 6A capsular polysaccharide of the invention is conjugated to the carrier protein (e.g. CRM-197) using CDAP chemistry. In one aspect, the CDAP chemistry uses a CDAP:PS6A ratio between 1:2 to 3:1, 1:1.5 to 2:1, e.g. 1:1. In another aspect, the CDAP conjugation is carried out using a coupling time of between 50-130 minutes, 60-130 minutes, or 110-130 minutes. Thus the present invention also provides, a process for preparing a *Streptococcus pneumoniae* serotype 6A capsular polysaccharide conjugate (e.g. a sized *Streptococcus pneumoniae* serotype 6A capsular polysaccharide of the invention) comprising conjugating a sized *Streptococcus pneumoniae* serotype 6A capsular polysaccharide to a carrier protein (e.g. CRM-197) or to a linker (e.g. ADH) using CDAP chemistry using a CDAP:PS (polysaccharide) ratio between 1:2 to 3:1, 1:1.5 to 2:1, e.g. 1:1.

In another aspect, the present invention provides, a process for preparing a *Streptococcus pneumoniae* serotype 6A capsular polysaccharide conjugate (e.g. a sized *Streptococcus pneumoniae* serotype 6A capsular polysaccharide of the invention) comprising conjugating a sized *Streptococcus pneumoniae* serotype 6A capsular polysaccharide to a carrier protein (e.g. CRM-197) using CDAP chemistry using a CDAP:PS (polysaccharide) ratio between 1:2 to 3:1, 1:1.5 to 2:1, e.g. 1:1. In one aspect, the present invention also provides, a process for preparing a *Streptococcus pneumoniae* serotype 6A capsular polysaccharide conjugate (e.g. a sized *Streptococcus pneumoniae* serotype 6A capsular polysaccharide of the invention, such as a *Streptococcus pneumoniae* serotype 6A capsular polysaccharide having an average size (e.g. $M_w$) between 100-1000, 110-750, 150-500, 180-600, 210-490, 210-450, 180-400, 210-400, 210-370, 220-360, 230-350, 240-340, 240-320, 240-310 or 250-310 kDa) comprising conjugating a sized *Streptococcus pneumoniae* serotype 6A capsular polysaccharide to a carrier protein (e.g. CRM-197) or to a linker (e.g. ADH) using CDAP chemistry using a coupling time of between 50-130 minutes, 60-130 minutes, or 110-130 minutes.

In another aspect, the present invention provides, a process for preparing a *Streptococcus pneumoniae* serotype 6A capsular polysaccharide conjugate (e.g. a sized *Streptococcus pneumoniae* serotype 6A capsular polysaccharide of the invention, such as a *Streptococcus pneumoniae* serotype 6A capsular polysaccharide having an average size (e.g. $M_w$) between 100-1000, 110-750, 150-500, 180-600, 210-490, 210-450, 180-400, 210-400, 210-370, 220-360, 230-350, 240-340, 240-320, 240-310 or 250-310 kDa) comprising conjugating a sized *Streptococcus pneumoniae* serotype 6A capsular polysaccharide to a carrier protein (e.g. CRM-197) using CDAP chemistry using a coupling time of between 50-130 minutes, 60-130 minutes, or 110-130 minutes. In one aspect, the pH for activation and coupling is between pH 8 to pH9, suitably pH9.5. In another aspect, the conjugation is carried out in the presence of NaCl. For example, in 0.1-3M NaCl, 0.1-2.5M NaCl, 1.5-2.5M NaCl or 2M NaCl.

The present invention also provides, a process for preparing a *Streptococcus pneumoniae* serotype 6A capsular polysaccharide conjugate comprising (a) conjugation of a *Streptococcus pneumoniae* serotype 6A capsular polysaccharide (e.g. a sized *Streptococcus pneumoniae* serotype 6A capsular polysaccharide of the invention) to a carrier protein (e.g. CRM-197) and (b) diafiltration against a solution having a concentration of NaCl below 150 mM (e.g. below 100 mM NaCl, below 50 mM NaCl, below 10 mM NaCl) or using water (e.g. WFI, water for injection).

In another aspect, the present invention provides, a solution comprising 6A-CRM197 in less than 150 mM NaCl. For example, less than 100 mM NaCl, less than 50 mM NaCl, less than nM NaCl, or in the absence of sodium chloride. In another aspect, the present invention provides, an immunogenic composition of the invention (e.g. 6A-CRM197) comprising less than 150 mM NaCl. For example, less than 100 mM NaCl, less than 50 mM NaCl, less than 10 mM NaCl, or in the absence of sodium chloride.

Ratio of Carrier Protein to Polysaccharide In an embodiment, the ratio of carrier protein to *S. pneumoniae* polysaccharide is between 1:5 and 5:1; e.g. between 1:0.5-4:1, 1:1-3.5:1, 1.2:1-3:1, 1.5:1-2.5:1; e.g. between 1:2 and 2.5:1; 1:1 and 2:1 (w/w; weight/weight). In an embodiment, the majority of the conjugates, for example 6, 7, 8, 9 or more of the conjugates have a ratio of carrier protein to polysaccharide that is greater than 1:1, for example 1.1:1, 1.2:1, 1.3:1, 1.4:1, 1.5:1 or 1.6:1.

In an embodiment, the ratio of carrier protein to *Streptococcus pneumoniae* serotype 6A capsular polysaccharide in immunogenic compositions of the invention is between 5:1 and 1:5, 4:1 and 1:1 or 2:1 and 1:1, 1.5:1 and 1:1, 1.4:1 and 1.3:1 (for example 1.2:1, 1.5:1) (w/w).

The ratio of polysaccharide to carrier protein (w/w) in a conjugate may be determined using the conjugate. The amount of protein is determined using a Lowry assay (for example Lowry et al. (1951) J. Biol. Chem. 193, 265-275 or Peterson et al. Analytical Biochemistry 100, 201-220 (1979)) and the amount of polysaccharide is determined using resorcinol assay (Monsigny et al. (1988) Anal. Biochem. 175, 525-530). The final Protein/Polysaccharide ratio (w/w) on the sterilized conjugate is determined by the ratio of the Lowry/resorcinol concentrations.

Size of Capsular Polysaccharides in the Immunogenic Composition

Capsular polysaccharides of *Streptococcus pneumoniae* comprise repeating oligosaccharide units which may contain up to 8 sugar residues. For a review of the oligosaccharide units for the key *Streptococcus pneumoniae* serotypes see JONES, Christopher. Vaccines based on the cell surface carbohydrates of pathogenic bacteria. *An. Acad. Bras. Ciênc.*, June 2005, vol. 77, no.2, p.293-324. Table II ISSN 0001-3765. In one embodiment, a capsular polysaccharide may be a full length polysaccharide, however in others it may be a shorter than native length polysaccharide chain of repeating units. In one embodiment, the *Streptococcus pneumoniae* serotype capsular polysaccharide conjugates post conjugation should be readily filterable through a 0.2 micron filter such that a yield of more than 95% is obtained post filtration compared with the pre filtration sample.

In addition to the sized *Streptococcus pneumoniae* serotype 6A capsular polysaccharide conjugate of the invention, the immunogenic composition of the invention may comprise one or more (poly)saccharide conjugates from *Streptococcus pneumoniae* serotypes other than 6A (e.g. 6B and/or 23F) wherein the average size (e.g. weight-average molecular weight; $M_w$) of the (poly)saccharide before conjugation is above 80 kDa, 100 kDa, 200 kDa, 300 kDa, 400 kDa, 500 kDa, 700 kDa or 1000 kDa. For example, the immunogenic composition of the invention may comprise one or more (poly)saccharide conjugates from *Streptococcus pneumoniae* serotypes other than 6A wherein the average size (e.g. weight-average molecular weight; $M_w$) of the (poly)saccharide before conjugation is between 80-100 kDa, 100-200 kDa, 200-300 kDa, 300-400 kDa, 400-500 kDa, 500-1000 kDa or 1000-1400 kDa. In one embodiment, the immunogenic composition comprises (i) sized a *Streptococcus pneumoniae* serotype 6A capsular polysaccharide conjugate and (ii) one or more (poly)saccharide conjugates with an average size of saccharide before conjugation of 50-1600, 80-1400, 100-1000, 150-500, or 200-400 kDa (note that where average size is $M_w$, 'kDa' units should be replaced herein with 'x10³').

In an embodiment, the immunogenic composition of the invention comprises a serotype 1 *S. pneumoniae* polysaccharide having an average size ($M_w$) of between 100-1000, 200-800, 250-600, or 300-400 kDa. In an embodiment, the immunogenic composition of the invention comprises a serotype 4 *S. pneumoniae* polysaccharide having an average size ($M_w$) of between 50-500, 60-300, 70-150, or 75-125 kDa. In an embodiment, the immunogenic composition of the invention comprises a serotype 5 *S. pneumoniae* polysaccharide having an average size ($M_w$) of between 100-1000, 100-700, 100-350, or 150-300 kDa. In an embodiment, the immunogenic composition of the invention comprises a serotype 6B *S. pneumoniae* polysaccharide having an average size ($M_w$) of between 200-1800, 500-1800, 600-1800, 900-1660, or 1000-1400 kDa. In an embodiment, the immunogenic composition of the invention comprises a serotype 7F *S. pneumoniae* polysaccharide having an average size ($M_w$) of between 50-1000, 100-750, 150-500, or 200-300 kDa. In an embodiment, the immunogenic composition of the invention comprises a serotype 9V *S. pneumoniae* polysaccharide having an average size ($M_w$) of between 50-1000, 100-750, 150-500, 200-400, or 250-300 kDa. In an embodiment, the immunogenic composition of the invention comprises a serotype 14 *S. pneumoniae* polysaccharide having an average size ($M_w$) of between 50-1000, 100-750, 150-500, or 200-250 kDa. In an embodiment, the immunogenic composition of the invention comprises a 18C *S. pneumoniae* polysaccharide having an average size ($M_w$) of between 50-1000, 50-750, 50-500, 50-190, 50-150 or 80-110 kDa. In an embodiment, the immunogenic composition of the invention comprises a 19A *S. pneumoniae* polysaccharide having an average size ($M_w$) of between 50-800, 110-700, 110-300, 120-200, 130-180, 140-160 or 80-130 kDa. In an embodiment, the immunogenic composition of the invention comprises a serotype 19F *S. pneumoniae* polysaccharide having an average size ($M_w$) of between 50-1000, 100-750, 100-500, 100-190 or 120-180 kDa. In an embodiment, the immunogenic composition of the invention comprises a serotype 23F *S. pneumoniae* polysaccharide having an average size ($M_w$) of between 500-1500, 600-1500, 700-1300, 900-1250, 800-1100, or 900-1000 kDa. In an embodiment, the immunogenic composition of the invention comprises a serotype 22F *S. pneumoniae* polysaccharide having an average size ($M_w$) of between 50-800, 110-700, 110-300, 120-200, 130-180, 150-170, 100-190, 100-150, 95-125 or 100-115 kDa.

In an embodiment, the immunogenic composition of the invention comprises 1 or more, native capsular polysaccharides from different *S. pneumoniae* serotypes. In another embodiment, the immunogenic composition comprises *Streptococcus pneumoniae* polysaccharides from at least 10 serotypes conjugated to a carrier protein, wherein at least 1, 2, 3, 4, 5, 6, 7, 8, or 9 of the *S. pneumoniae* polysaccharide serotypes is native polysaccharide. In another embodiment, the immunogenic composition of the invention comprises native *Streptococcus pneumoniae* capsular serotype 6B polysaccharide. In another embodiment, the immunogenic composition of the invention comprises native *Streptococcus pneumoniae* capsular serotype 23F polysaccharide.

In an aspect of the invention, the immunogenic composition comprises *Streptococcus pneumoniae* polysaccharides from at least 10 serotypes conjugated to a carrier protein, wherein at least 1, 2, 3, 4, 5, 6, 7, 8, or 9 of the *S. pneumoniae* polysaccharide serotypes is sized by a factor up to ×2, ×3, ×4, ×5, ×6, ×7, ×8, ×9 or ×10. In one embodiment of this aspect, the majority of the polysaccharides, for example 6, 7, 8 or more of the polysaccharide serotypes are sized by a factor up to ×2, ×3, ×4, ×5, ×6, ×7, ×8, ×9 or ×10. For example, sizing may be from a factor of between ×2 to ×6, ×2 to ×5, ×2 to ×4, or ×3 to ×6, ×3 to ×5 or ×3 to ×4.

In an embodiment, the majority of *S. pneumoniae* polysaccharides in the immunogenic composition are sized. In an embodiment, the majority of *S. pneumoniae* polysaccharide serotypes in the immunogenic composition are sized. In one aspect, *S. pneumoniae* polysaccharides in the immunogenic composition are sized mechanical cleavage, for instance by microfluidisation or sonication. In another aspect, *S. pneumoniae* polysaccharides in the immunogenic composition are sized by chemical cleavage, e.g. treatment with acetic acid or periodate. Sizing is by a factor of no more than ×20, ×10, ×8, ×6, ×5, ×4, ×3 or ×2.

In an embodiment, the immunogenic composition comprises S. pneumoniae conjugates that are a mixture of native polysaccharides and polysaccharides that are sized by a factor of no more than ×20, ×10, ×8, ×6, ×5, ×4, ×3 or ×2. In one aspect of this embodiment, the majority of the polysaccharides, for example 6, 7, 8, 9, 10 or more of the polysaccharides are sized by a factor of up to ×2, ×3, ×4, ×5 or ×6.

Dosage

In general, the immunogenic composition of the invention may comprise a dose of each saccharide conjugate between 0.1 and 20 μg, 1 and 10 μg or 1 and 3 μg of saccharide.

In an embodiment, in the immunogenic composition of the present invention the dose of the Streptococcus pneumoniae 6A polysaccharide conjugate is between 1 and 10 μg, 1 and 5 μg, or 1 and 3 μg of saccharide (e.g. 2 μg).

In an embodiment, the immunogenic composition of the invention contains each S. pneumoniae capsular saccharide at a dose of between 0.1-20 μg; 0.5-10 μg; 0,5-5 μg or 1-3 μg of saccharide. In an embodiment, capsular polysaccharides may be present at different dosages, for example some capsular polysaccharides may be present at a dose of around or exactly 1 μg or some capsular polysaccharides may be present at a dose of around or exactly 3 μg. In an embodiment, polysaccharides from serotypes 3, 18C and 19F are present at a higher dose than other polysaccharides. In an embodiment, polysaccharides from serotypes 4, 18C and 19F are present at a higher dose than other polysaccharides. In one aspect of this embodiment, serotypes 3, 18C and 19F are present at a dose of around or exactly 3 μg whilst other polysaccharides in the immunogenic composition are present at a dose of around or exactly 1 μg. In one aspect of this embodiment, serotypes 4, 18C and 19F are present at a dose of around or exactly 3 μg whilst other polysaccharides in the immunogenic composition are present at a dose of around or exactly 1 μg.

"Around" or "approximately" are defined as within 10% more or less of the given figure for the purposes of the invention.

Streptococcus pneumoniae Proteins

The immunogenic composition of the invention may also comprise Streptococcus pneumoniae proteins, herein termed Streptococcus pneumoniae proteins of the invention.

Such proteins may be used as carrier proteins, or may be present as free proteins, or may be present both as carrier proteins and as free proteins. In an embodiment, the immunogenic composition of the invention further comprises one or more unconjugated or conjugated S. pneumoniae proteins. In an embodiment, the immunogenic composition of the invention further comprises one or more unconjugated S. pneumoniae proteins. For example, immunogenic compositions of the invention may comprise unconjugated pneumolysin, e.g. dPly, and unconjugated pneumococcal PhtD.

The Streptococcus pneumoniae proteins of the invention are either surface exposed, at least during part of the life cycle of the pneumococcus, or are proteins which are secreted or released by the pneumococcus. In an embodiment, the proteins of the invention are selected from the following categories, such as proteins having a Type II Signal sequence motif of LXXC (where X is any amino acid, e.g., the polyhistidine triad family (PhtX)), choline binding proteins (e.g. CbpX, PcpA), proteins having a Type I Signal sequence motif (e.g., Sp101), proteins having a LPXTG (SEQ ID NO: 4) motif (where X is any amino acid, e.g., Sp128, Sp130), and toxins (e.g., Ply). Preferred examples within these categories (or motifs) are the following proteins, or immunologically functional equivalents thereof. Thus, the immunogenic composition of the invention may comprise one or more S. pneumoniae proteins selected from Poly Histidine Triad family (PhtX), Choline Binding Protein family (CbpX), CbpX truncates, pneumococcal autolysin LytX family (LytA (N-acetylmuramoyl-l-alanine amidase), LytB, LytC), LytX truncates, CbpX truncate-LytX truncate chimeric proteins, detoxified pneumolysin (Ply), PspA, PsaA, Sp128, Sp101, Sp130, Sp125 and Sp133. In a further embodiment, the immunogenic composition of the invention comprises 2 or more proteins selected from the group consisting of the Poly Histidine Triad family (PhtX), Choline Binding Protein family (CbpX), CbpX truncates, LytX family, LytX truncates, CbpXtruncate-LytXtruncate chimeric proteins (or fusions), pneumolysin (Ply), PspA, PsaA, and Sp128. In a further embodiment, the immunogenic composition comprises 2 or more proteins selected from the group consisting of the Poly Histidine Triad family (PhtX), Choline Binding Protein family (CbpX), CbpX truncates, LytX family, LytX truncates, CbpX truncate-LytX truncate chimeric proteins (or fusions), pneumolysin (Ply), and Sp128.

The Pht (Poly Histidine Triad) family comprises proteins PhtA, PhtB, PhtD, and PhtE. The family is characterized by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and Neisseria. In one embodiment of the invention, the immunogenic composition comprises PhtD. It is understood, however, that the terms Pht A, B, D, and E refer to proteins having sequences disclosed in the citations below as well as variants thereof that have a sequence homology that is at least 90% identical to the proteins described below, e.g. amino acids 21-838 of SEQ ID NO: 4 of WO00/37105. In an embodiment it is at least 95% identical and in another embodiment it is 97% identical.

With regards to the PhtX proteins, PhtA is disclosed in WO 98/18930, and is also referred to Sp36. As noted above, it is a protein from the polyhistidine triad family and has the type II signal motif of LXXC. PhtD is disclosed in WO 00/37105, and is also referred to Sp036D. As noted above, it also is a protein from the polyhistidine triad family and has the type II LXXC signal motif. PhtB is disclosed in WO 00/37105, and is also referred to Sp036B. Another member of the PhtB family is the C3-Degrading Polypeptide, as disclosed in WO 00/17370. This protein also is from the polyhistidine triad family and has the type II LXXC signal motif. A preferred immunologically functional equivalent is the protein Sp42 disclosed in WO 98/18930. A PhtB truncate (approximately 79 kD) is disclosed in WO99/15675 which is also considered a member of the PhtX family. PhtE is disclosed in WO00/30299 and is referred to as BVH-3. Where any Pht protein is referred to herein, it is meant that immunogenic fragments or fusions thereof of the Pht protein can be used. For example, a reference to PhtX includes immunogenic fragments or fusions thereof from any Pht protein.

In one embodiment, the S. pneumoniae protein selected from member(s) of the Polyhistidine Triad family is PhtD. The term "PhtD" as used herein includes the full length protein with the signal sequence attached or the mature full length protein with the signal peptide (for example 20 amino acids at N-terminus) removed, and immunogenic fragments, variants and/or fusion proteins thereof, e.g. SEQ ID NO: 4 of WO00/37105. In one aspect, PhtD is the full length protein with the signal sequence attached e.g. SEQ ID NO: 4 of WO00/37105. In another aspect, PhtD is a sequence comprising the mature full length protein with the signal peptide (for example 20 amino acids at N-terminus) removed, e.g. amino acids 21-838 of SEQ ID NO: 4 of WO00/37105. Suitably, the PhtD sequence comprises an N-terminal methionine. The present invention also includes PhtD polypeptides which are immunogenic fragments of PhtD, variants of PhtD and/or fusion proteins of PhtD. For example, as described in WO00/37105, WO00/39299, U.S. Pat. No. 6,699,703 and WO09/12588.

Where immunogenic fragments of PhtD proteins are used (separately or as part of a fusion protein), these immunogenic fragments will be at least about 15, at least about 20, at least about 40, or at least about 60 contiguous amino acid residues in length, e.g from a PhtD amino acid sequence in WO00/37105 or WO00/39299, such as SEQ ID NO: 4 of WO00/37105. In an embodiment of the invention, immunogenic fragments of PhtD protein comprise at least about 15, at least about 20, at least about 40, or at least about 60 contiguous amino acid residues of the sequence shown in SEQ ID NO: 4 of WO00/37105, wherein said polypeptide is capable of eliciting an immune response specific for said amino acid sequence. In an embodiment, the immunogenic composition of the invention comprises an immunogenic fragment of PhtD, for example described in WO09/12601, WO01/98334 and WO09/12588. Where immunogenic fragments of PhtD proteins are used (separately or as part of a fusion protein), each immunogenic fragment optionally contains one or more histidine triad motif(s) of such polypeptides. A histidine triad motif is the portion of polypeptide that has the sequence HxxHxH where H is histidine and x is an amino acid other than histidine. In an embodiment of the present invention, the or each immunogenic fragment contains exactly or at least 2, 3, 4 or 5 histidine triad motifs (optionally, with native PhtD sequence between the 2 or more triads, or intra-triad sequence) where the immunogenic fragment is more than 50, 60, 70, 80, 90 or 100% identical to a native pneumococcal intra-triad PhtD sequence (e.g. the intra-triad sequence shown in SEQ ID NO: 4 of WO00/37105). Immunogenic fragments of PhtD proteins optionally contain one or more coiled coil regions of such polypeptides. A coiled coil region is a region predicted by "Coils" algorithm Lupus, A et al (1991) Science 252; 1162-1164. In an embodiment of the present invention, each immunogenic fragment contains exactly or at least 2, 3 or 4 coiled coil regions. In an embodiment of the present invention, the or each immunogenic fragment contains exactly or at least 2, 3 or 4 coiled coil regions where the immunogenic fragment is more than 50, 60, 70, 80, 90, 95, 96 or 100% identical to a native pneumococcal PhtD sequence (e.g. the sequence shown in SEQ ID NO: 4 of WO00/37105). In another embodiment of the present invention, the immunogenic fragment includes one or more histidine triad motif as well as at least 1, 2, 3 or 4 coiled coil regions.

In the case where the PhtD polypeptide is a variant, the variation is generally in a portion thereof other than the histidine triad residues and the coiled-coil region, although variations in one or more of these regions may be made. In accordance with the present invention, a polypeptide variant includes sequences in which one or more amino acids are substituted and/or deleted and/or inserted compared to the wild type sequence. Amino acid substitution may be conservative or non-conservative. In one aspect, amino acid substitution is conservative. Substitutions, deletions, insertions or any combination thereof may be combined in a single variant so long as the variant is an immunogenic polypeptide. Variants of PhtD typically include any immunogenic fragment or variation of PhtD which shares at least 80, 90, 95, 96, 98, or 99% amino acid sequence identity with a wild-type PhtD sequence, e.g. SEQ ID NO: 4 of WO00/37105. In an embodiment, the present invention includes immunogenic fragments and/or variants in which several, 5 to 10, 1 to 5, 1 to 3, 1 to 2 or 1 amino acid(s) are substituted, deleted, or added in any combination. In another embodiment, the present invention includes immunogenic fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]).

In an embodiment of the invention, PhtD and its immunogenic fragments, variants and/or fusion proteins thereof comprise an amino acid sequence sharing at least 80, 85, 90, 95, 96, 97, 98, 99 or 100% identity with amino acid sequence 21 to 838 of SEQ ID NO:4 of WO00/37105. In another embodiment of the invention, PhtD and its immunogenic fragments, variants and/or fusion proteins thereof have an amino acid sequence sharing at least 80, 85, 90, 95, 96, 97, 98, 99 or 100% identity with amino acid sequence 21 to 838 of SEQ ID NO:4 of WO00/37105. Suitably, PhtD and its immunogenic fragments, variants and/or fusion proteins thereof comprise an amino acid sequence having an N-terminal methionine. In another embodiment of the invention, PhtD and its immunogenic fragments, variants and/or fusion proteins thereof comprise at least about 15, at least about 20, at least about 40, or at least about 60 or at least about 100, or at least about 200, or at least about 400 or at least about 800 contiguous amino acid residues of the sequence shown in SEQ ID NO: 4 of WO00/37105.

Pneumolysin (Ply) is a multifunctional toxin with a distinct cytolytic (hemolytic) and complement activation activities (Rubins et al., Am. Respi. Cit Care Med, 153: 1339-1346 (1996)). The toxin is not secreted by pneumococci, but it is released upon lysis of pneumococci under the influence of autolysin. Its effects include e.g., the stimulation of the production of inflammatory cytokines by human monocytes, the inhibition of the beating of cilia on human respiratory epithelial, the decrease of bactericidal activity and migration of neutrophils, and in the lysis of red blood cells, which involves binding to cholesterol. Because it is a toxin, it needs to be detoxified (i.e., non-toxic to a human when provided at a dosage suitable for protection) before it can be administered in vivo. Expression and cloning of wild-type or native pneumolysin is known in the art. See, for example, Walker et al. (Infect Immun, 55:1184-1189 (1987)), Mitchell et al. (Biochim Biophys Acta, 1007:67-72 (1989) and Mitchell et al (NAR, 18:4010 (1990)). Detoxification of Ply can be conducted by chemical means, e.g., subject to formalin or glutaraldehyde treatment or a combination of both (WO 04081515, PCT/EP2005/010258). Such methods are known in the art for various toxins. Alternatively, Ply can be genetically detoxified. Thus, the invention encompasses derivatives of pneumococcal proteins which may be, for example, mutated proteins. The term "mutated" is used herein to mean a molecule which has undergone deletion, addition or substitution of one or more amino acids using known techniques for site directed mutagenesis or any other conventional method. For example, as described above, a mutant Ply protein may be altered so that it is biologically inactive whilst still maintaining its immunogenic epitopes, see, for example, WO90/06951, Berry et al. (Infect Immun, 67:981-985 (1999)) and WO99/03884.

As used herein, it is understood that the term "Ply" encompasses mutated pneumolysin and detoxified pneumolysin (dPly) suitable for medical use (i.e., non toxic).

Concerning the Choline Binding Protein family (CbpX), members of that family were originally identified as pneumococcal proteins that could be purified by choline-affinity chromatography. All of the choline-binding proteins are non-covalently bound to phosphorylcholine moieties of cell wall teichoic acid and membrane-associated lipoteichoic acid. Structurally, they have several regions in common over the entire family, although the exact nature of the proteins (amino acid sequence, length, etc.) can vary. In general, choline binding proteins comprise an N terminal region (N), conserved repeat regions, a proline rich region (P) and a conserved choline binding region (C), made up of multiple repeats, that comprises approximately one half of the protein. As used in this application, the term "Choline Binding Protein family (CbpX)" is selected from the group consisting of Choline Binding Proteins as identified in WO97/41151, Choline binding protein A, CbpA (also referred to as PbcA (C3-binding protein A), SpsA (*Streptococcus pneumoniae* secretory IgA binding protein), PspC (pneumococcal surface protein C)), Choline binding protein D (CbpD), and Choline binding protein G (CbpG). CbpA is disclosed in WO97/41151. CbpD and CbpG are disclosed in WO00/29434. PspC is disclosed in WO97/09994. PbcA is disclosed in WO98/21337. SpsA is a Choline binding protein disclosed in WO 98/39450. In an embodiment, the Choline Binding Proteins is CbpA. Another Choline Binding Protein is pneumococcal choline-binding protein A (PcpA) (Sanchez-Beato et al FEMS Microbiology Letters 164 (1998) 207-214).

Another preferred embodiment is CbpX truncates wherein "CbpX" is CbpA, CbpD or CbpG and "truncates" refers to CbpX proteins lacking 50% or more of the Choline binding region (C). Another preferred embodiment is PcpA truncates wherein "truncates" refers to PcpA proteins lacking 50% or more of the Choline binding region (C). In an embodiment, CbpX truncates or PcpA truncates lack the entire choline binding region. In another embodiment, the CbpX truncates or PcpA truncates lack (i) the choline binding region and (ii) a portion of the N-terminal half of the protein as well, yet retain at least one repeat region. In another embodiment, the truncate has at least 2 repeat regions. Examples of such preferred embodiments are illustrated in WO99/51266 or WO99/51188, however, other choline binding proteins lacking a similar choline binding region are also contemplated within the scope of this invention.

The LytX family is membrane associated proteins associated with cell lysis. The N-terminal domain comprises choline binding domain(s), however the LytX family does not have all the features found in the CbpA family noted above and thus for the present invention, the LytX family is considered distinct from the CbpX family. In contrast with the CbpX family, the C-terminal domain contains the catalytic domain of the LytX protein family. The family comprises LytA, LytB and LytC. With regards to the LytX family, LytA is disclosed in Ronda et al., Eur J Biochem, 164:621-624 (1987). LytB is disclosed in WO 98/18930, and is also referred to as Sp46. LytC is also disclosed in WO 98/18930, and is also referred to as Sp91. A preferred member of that family is LytC.

Another preferred embodiment are LytX truncates wherein "LytX" is LytA, LytB or LytC and "truncates" refers to LytX proteins lacking 50% or more of the Choline binding region. Suitably such proteins lack the entire choline binding region. Yet another preferred embodiment of this invention are CbpX truncate-LytX truncate chimeric proteins (or fusions). In an embodiment, the CbpX truncate-LytX truncate chimeric protein comprises the repeat regions of CbpX and the C-terminal portion (Cterm, i.e., lacking the choline binding domains) of LytX (e.g., LytCCterm or Sp91Cterm). In another embodiment, CbpX is selected from the group consisting of CbpA, PbcA, SpsA and PspC. In another embodiment, it is CbpA. In an embodiment, LytX is LytC (also referred to as Sp91). Another embodiment of the present invention is a PspA or PsaA truncates lacking the choline binding domain (C) and expressed as a fusion protein with LytX. In an embodiment, LytX is LytC.

PsaA and transmembrane deletion variants thereof have been described by Berry & Paton, Infect Immun 1996 Dec; 64(12):5255-62. PsaA and transmembrane deletion variants thereof have been disclosed in, for example, U.S. Pat. No. 5,804,193, WO 92/14488, and WO 99/53940.

Sp128 and Sp130 are disclosed in WO00/76540. Sp125 is an example of a pneumococcal surface protein with the Cell Wall Anchored motif of LPXTG (SEQ ID NO: 4) (i.e. leucine-proline-X-threonine-glycine where X is any amino acid). Any protein within this class of pneumococcal surface protein with this motif has been found to be useful within the context of this invention, and is therefore considered a further protein of the invention. Sp125 itself is disclosed in WO 98/18930, and is also known as ZmpB—a zinc metalloproteinase. Sp101 is disclosed in WO 98/06734 (where it has the reference #y85993). It is characterized by a Type I signal sequence. Sp133 is disclosed in WO 98/06734 (where it has the reference #y85992). It is also characterized by a Type I signal sequence.

The proteins of the invention may also be beneficially combined. By combined is meant that the immunogenic composition comprises all of the proteins from within the following combinations, either as carrier proteins or as free proteins or a mixture of the two. For example, in a combination of two proteins as set out hereinafter, both proteins may be used as carrier proteins, or both proteins may be present as free proteins, or both may be present as carrier and as free protein, or one may be present as a carrier protein and a free protein whilst the other is present only as a carrier protein or only as a free protein, or one may be present as a carrier protein and the other as a free protein. Where a combination of three proteins is given, similar possibilities exist. Preferred combinations include, but are not limited to PhtD+CbpX repeat regions, PhtD+Ply, PhtD+Sp128, PhtD+PsaA, PhtD+PspA, PhtA+CbpX repeat regions, PhtA+CbpX repeat regions —Sp91Cterm chimeric or fusion proteins, PhtA+Ply, PhtA+Sp128, PhtA+PsaA, PhtA+PspA, CbpX repeat regions+LytC, CbpX repeat regions+PspA, CbpX repeat regions+PsaA, CbpX repeat regions+Sp128, CbpX repeat regions+LytC, CbpX repeat regions+PspA, CbpX repeat regions+PsaA, CbpX repeat regions+Sp128, CbpX repeat regions+PhtD, CbpX repeat regions+PhtA. In an embodiment, CbpX repeat regionsis from CbpA. In another embodiment, it is from CbpA. Other combinations include 3 protein combinations such as PhtD+CbpX repeat regions+Ply, and PhtA+CbpX repeat regions+PhtD. In one embodiment, the immunogenic composition comprises detoxified pneumolysin and PhtD or PhtDE as carrier proteins. In a further embodiment, the immunogenic composition comprises detoxified pneumolysin and PhtD or PhtDE as free proteins.

The total content of protein antigens in the vaccine will typically be in the range 1-100 μg, or 5-80 μg, e.g. in the range 50-70 μg. For example, in one aspect, the immunogenic composition of the invention comprises 26 μg-45 μg (for example 26 μg-40 μg, 28 μg-35 μg or around 30 μg) of each S. pneumoniae protein, per human dose. In another aspect, the immunogenic composition comprises 26 μg-45 μg (for example 26 μg-40 μg, 28 μg-35 μg or around 30 μg) of PhtD, per human dose. In another aspect, the immunogenic composition of the invention comprises 26 μg-45 μg (for example 26 μg-40 μg, 28 μg-35 μg or around 30 μg) of pneumolysin (e.g. dPly), per human dose.

By the term "human dose" is meant a dose which is in a volume suitable for human use. Generally this is between 0.25 and 1.5 ml. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the paediatric population, a human dose may be less than 0.5 ml such as between 0.25 and 0.5 ml.

Adjuvants

The immunogenic compositions of the present invention may be adjuvanted, particularly when intended for use in an elderly population but also for use in infant populations. Thus, a further aspect is an immunogenic composition of the invention which further comprises an adjuvant. Suitable adjuvants include an aluminum salt such as aluminum hydroxide gel or aluminum phosphate or alum, but a suitable adjuvant may also be a salt of calcium, magnesium, iron or zinc, or may be an insoluble suspension of acylated tyrosine, or acylated sugars, cationically or anionically derivatized polysaccharides, or polyphosphazenes. In one aspect of the invention, the adjuvant is an aluminium salt, e.g. aluminium phosphate. In a further aspect, the adjuvant comprises (per 0.5 mL dose) 100-750, 200-500, or 300-400 μg Al (aluminium) as aluminium phosphate.

In one embodiment, the adjuvant is a preferential inducer of a Th1 type of response. Such high levels of Th1-type cytokines tend to favour the induction of cell mediated immune responses to a given antigen, whilst high levels of Th2-type cytokines tend to favour the induction of humoral immune responses to the antigen. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, suitably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-61].

The immunogenic composition may comprise a sized Streptococcus pneumoniae serotype 6A capsular polysaccharide (and optionally an immunostimulant) adsorbed onto a metal salt (such as an aluminium salt, for example Aluminium phosphate or Aluminium hydroxide). The term "immunostimulant" as used herein means a substance that stimulates an immune response, in particular an adjuvant which stimulates the immune system of a host animal (e.g. human) to which it is administered and thereby increases the protective effect produced by a antigen administered to that animal, as compared to the effect which would be produced by administration of the antigen alone. For aluminium based vaccine formulations wherein the antigen is typically adsorbed onto aluminium salt for one hour at room temperature under agitation.

Adjuvants Comprising Additional Immunostimulants

The adjuvant of the invention may comprise immunostimulants, such as saponins (e.g. QS21) and/or 3D-MPL. Examples of immunostimulants are described herein and in "Vaccine Design—The Subunit and Adjuvant Approach" 1995, Pharmaceutical Biotechnology, Volume 6, Eds. Powell, M. F., and Newman, M. J., Plenum Press, New York and London, ISBN 0-306-44867-X. In one aspect of the present invention the adjuvant comprises QS21, monophosphoryl lipid A (MPL), phospholipid and sterol, presented in the form of a liposome.

QS-21 is a purified saponin fraction from the bark extracts of the South American tree Quillaja saponaria. QS21 typically comprises two principal isomers that share a triterpene, a branched trisaccharide, and a glycosylated pseudodimeric acyl chain. The two isomeric forms differ in the constitution of the terminal sugar within the linear tetrasaccharide segment, wherein the major isomer, QS-21-Api incorporates a β-D-apiose residue, and the minor isomer, QS-21-Xyl terminates in a β-D-xylose substituent. (Cleland, J. L. et al. J. Pharm. Sci. 1996, 85, 22-28). QS21 may be prepared by HPLC purification from Quil A™. Quil A™ was described as having adjuvant activity by Dalsgaard et al. in 1974 ("Saponin adjuvants", Archiv. für die gesamte Virusforschung, Vol. 44, Springer Verlag, Berlin, p243-254). Methods for production of QS21 are described in U.S. Pat. No. 5,057,540 (where QS21 is described as QA21) and EP0362278. In an embodiment, immunogenic compositions of the invention contain QS21 in substantially pure form, that is to say, the QS21 comprises at least 90%, for example at least 95%, or at least 98% of the immunogenic composition (i.e. the QS21 composition contains at least 90%, for example at least 95%, or at least 98% QS21). The dose of QS21 is suitably able to enhance an immune response to an antigen in a human. In particular a suitable QS21 amount is that which improves the immunological potential of the composition compared to the unadjuvanted composition, or compared to the composition adjuvanted with another QS21 amount, whilst being acceptable from a reactogenicity profile. QS21 can be used, for example, at an amount of 1 to 100 μg per composition dose, for example in an amount of 10 to 50 μg per composition dose.

Monophosphoryl lipid A (MPL) is a nontoxic derivative of the lipopolysaccharide (LPS) of gram-negative bacteria, e.g. Salmonella minnesota R595. It retains adjuvant properties of the LPS while demonstrating a reduced toxicity (Johnson et al. 1987 Rev. Infect. Dis. 9 Suppl:S512-S516). MPL is composed of a series of 4'-monophosphoryl lipid A species that vary in the extent and position of fatty acid substitution. It may be prepared by treating LPS with mild acid and base hydrolysis followed by purification of the modified LPS. For example, LPS may be refluxed in mineral acid solutions of moderate strength (e.g. 0.1 M HCl) for a period of approximately 30 minutes. This process results in dephosphorylation at the 1 position, and decarbohydration at the 6' position. The term "monophosphoryl lipid A (MPL)" as used herein includes derivatives of monophosphoryl lipid A. Derivatives of monophosphoryl lipid A include 3D-MPL and synthetic derivatives. 3D-MPL is 3-O-deacylated monophosphoryl lipid A (or 3 De-O-acylated monophosphoryl lipid A). Chemically it is a mixture of 3—deacylated monophosphoryl lipid A with 4, 5 or 6 acylated chains. 3D—MPL is available under the trademark MPL® by GlaxoSmithKline Biologicals North America. 3-O-deacylated monophosphoryl lipid A (3D-MPL). It has a further reduced toxicity while again maintaining adjuvanticity, and may typically be prepared by mild alkaline hydrolysis, see for example U.S. Pat. No. 4,912,094. Alkaline hydrolysis is typically performed in organic solvent, such as a mixture of chloroform/methanol, by saturation with an aqueous solution of weak base, such as 0.5 M sodium carbonate at pH 10.5. For further information on the preparation of 3D-MPL see GB2220211A and WO02078637 (Corixa Corporation). In one aspect of the present invention small particle 3 D-MPL may be used. Small particle 3D-MPL has a particle size such that it may be sterile-filtered through a 0.22 µm filter. Such preparations are described in International Patent Application No. WO94/21292. In an embodiment, immunogenic compositions of the invention comprise 3-O-Deacylated monophosphoryl lipid A (3D-MPL).

The dose of monophosphoryl lipid A (MPL), e.g. 3D-MPL, is suitably able to enhance an immune response to an antigen in a human. In particular a suitable monophosphoryl lipid A (MPL), e.g. 3D-MPL, amount is that which improves the immunological potential of the composition compared to the unadjuvanted composition, or compared to the composition adjuvanted with another MPL amount, whilst being acceptable from a reactogenicity profile. Monophosphoryl lipid A (MPL), e.g. 3D-MPL, can be used, for example, at an amount of 1 to 100 µg per composition dose, for example in an amount of 10 to 50 µg per composition dose.

Liposomes may be made from phospholipids (such as dioleoyl phosphatidyl choline, DOPC) and sterol, e.g. cholesterol, using techniques known in the art. Such liposome carriers may carry the QS21 and/or monophosphoryl lipid A (MPL), e.g. 3D-MPL. Suitable compositions of the invention are those wherein liposomes are initially prepared without MPL (as described in WO96/33739), and MPL is then added, suitably as small particles of below 100 nm particles or particles that are susceptible to sterile filtration through a 0.22 µm membrane. The MPL is therefore not contained within the vesicle membrane (known as MPL out). Compositions where the MPL is contained within the vesicle membrane (known as MPL in) also form an aspect of the invention. The unconjugated S. pneumoniae proteins can be contained within the vesicle membrane or contained outside the vesicle membrane. Suitably soluble antigens are outside and hydrophobic or lipidated antigens are either contained inside or outside the membrane. Encapsulation within liposomes is described in U.S. Pat. No. 4,235,877.

The liposomes of the present invention may comprise a phospholipid, for example a phosphatidylcholine, which may be non-crystalline at room temperature, for example egg yolk phosphatidylcholine, dioleoyl phosphatidylcholine or dilauryl phosphatidylcholine. Suitably, the phospholipid is dioleoylphosphatidylcholine (DOPC). A further aspect is an immunogenic composition of the invention comprising 0.1 to 10 mg, 0.2 to 7, 0.3 to 5, 0.4 to 2, or 0.5 to 1 mg (e.g. 0.4 to 0.6, 0.9 to 1.1, 0.5 or 1 mg) phospholipid.

The liposomes of the present invention may comprise a sterol. The sterol increases the stability of the liposome structure. Suitable sterols include β-sitosterol, stigmasterol, ergosterol, ergocalciferol and cholesterol. These sterols are described in the art, for example cholesterol is disclosed in the Merck Index, 11th Edn., page 341, as a naturally occurring sterol found in animal fat. In one particular embodiment of the invention, the sterol is cholesterol. Typically, the sterol may be added during formulation of the antigen preparation using QS21 quenched with the sterol as described in WO96/33739. In an embodiment, the immunogenic compositions of the invention comprise 0.025 to 2.5, 0.05 to 1.5, 0.075 to 0.75, 0.1 to 0.3, or 0.125 to 0.25 mg (e.g. 0.2 to 0.3, 0.1 to 0.15, 0.25 or 0.125 mg) sterol.

In one embodiment the adjuvant comprises (per 0.5 mL dose) 0.1-10 mg, 0.2-7, 0.3-5, 0.4-2, or 0.5-1 mg (e.g. 0.4-0.6, 0.9-1.1, 0.5 or 1 mg) phospholipid (for instance DOPC), 0.025-2.5, 0.05-1.5, 0.075-0.75, 0.1-0.3, or 0.125-0.25 mg (e.g. 0.2-0.3, 0.1-0.15, 0.25 or 0.125 mg) sterol (for instance cholesterol), 5-60, 10-50, or 20-30 µg (e.g. 5-15, 40-50, 10, 20, 30, 40 or 50 µg) lipid A derivative (for instance 3D-MPL), and 5-60, 10-50, or 20-30 µg (e.g. 5-15, 40-50, 10, 20, 30, 40 or 50 µg)saponin (for instance QS21).

Liposomes of the invention will suitably be comprised in a liquid medium. The liquid medium comprises physiologically acceptable liquids such as water, aqueous salt solutions and buffer solutions, e.g phosphate buffered saline (PBS) etc. For example, immunogenic compositions of the invention may comprise water and PBS.

In one aspect of the invention, the adjuvant is ASO1B (see e.g. WO96/33739). In another aspect of the invention, the adjuvant is ASO1E (see e.g. WO2007/068907).

In some cases it may be advantageous that the immunogenic compositions and vaccines of the present invention will further contain a stabiliser, for example other emulsifiers/surfactants, including caprylic acid (Merck index 10th Edition, entry no. 1739), of which Tricaprylin is particularly preferred.

Oil in Water Emulsion Adjuvants

Oil in water emulsion adjuvants per se have been suggested to be useful as adjuvant compositions (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B). All of which form preferred oil emulsion systems (in particular when incorporating tocols) that are suitable as adjuvants for use in compositions of the present invention.

A suitable oil emulsion (for example an oil-in-water emulsion) comprises a metabolisable, non-toxic oil, such as squalane, a tocopherol such as alpha tocopherol and optionally an emulsifier (or surfactant) such as polysorbate 80 (TWEEN 80). A sterol (for example cholesterol) may also be included. In one aspect of the invention, there is provided a vaccine or immunogenic composition comprising a sized S. pnemoniae serotype 6A capsular polysaccharide and an adjuvant composition comprising an oil in water emulsion, wherein the oil in water emulsion comprises 0.5-11 mg metabolisable oil, (such as squalene), 0.5-12 mg tocol (such as alpha-tocopherol) and 0.4-5 mg emulsifying agent (such as polyoxyethylene sorbitan monooleate), per human dose.

In order for any oil in water composition to be suitable for human administration, the oil phase of the emulsion system has to comprise a metabolisable oil. The meaning of the term metabolisable oil is known in the art. Metabolisable can be defined as 'being capable of being transformed by metabolism' (Dorland's Illustrated Medical Dictionary, W. B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19,23-Hexamethyl-2,6,10, 14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil, that it is an intermediate in the biosynthesis of cholesterol (Merck index, 10th Edition, entry no.8619). Suitably the metabolisable oil is present in the adjuvant composition in an amount of 0.5-10 mg, for example 1-10, 2-10, 3-9, 4-8, 5-7, or 5-6 mg (e.g. 2-3, 5-6, or 9-10 mg).

The oil in water emulsion suitably comprises a tocol. Tocols are known in the art and are described in EP0382271. Suitably the tocol is alpha-tocopherol or a derivative thereof such as alpha-tocopherol succinate (also known as vitamin E succinate). Said tocol is suitably present in the adjuvant composition in an amount of 0.5-11 mg, for example 1-11, 2-10, 3-9, 4-8, 5-7, 5-6 (e.g. 10-11, 5-6, 2.5-3.5 or 1-3 mg). In a specific embodiment the tocol is present in an amount of 5.94 mg or 2.38 mg. In a further embodiment, said tocol is suitably present in the vaccine (or immunogenic) composition in an amount of 0.5-11 mg, for example 1-11, 2-10, 3-9, 4-8, 5-7, 5-6 (e.g. 10-11, 5-6, 2.5-3.5 or 1-3 mg).

The oil in water emulsion may further comprise an emulsifying agent. The emulsifying agent may suitably be polyoxyethylene sorbitan monooleate. In a particular embodiment the emulsifying agent may be selected from the group comprising: Polysorbate 80 (TWEEN 80). Said emulsifying agent is suitably present in the adjuvant composition in an amount of 0.1-5, 0.2-5, 0.3-4, 0.4-3 or 2-3 mg (e.g. 0.4-1.2, 2-3 or 4-5 mg) emulsifying agent.

The method of producing oil-in-water emulsions is known to the person skilled in the art. Commonly, the method comprises mixing the tocol-containing oil phase with a surfactant such as a PBS/TWEEN 80 solution, followed by homogenisation using a homogenizer. A method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion.

In an oil in water emulsion, the oil and emulsifier should be in an aqueous carrier. The aqueous carrier may be, for example, phosphate buffered saline.

In an embodiment, the oil-in-water emulsion systems of the present invention have a small oil droplet size in the sub-micron range. Suitably the droplet sizes will be in the range 120 to 750 nm, or from 120 to 600 nm in diameter. In an embodiment, the oil-in water emulsion contains oil droplets of which at least 70% by intensity are less than 500 nm in diameter, or at least 80% by intensity are less than 300 nm in diameter, or at least 90% by intensity are in the range of 120 to 200 nm in diameter.

The oil droplet size, i.e. diameter, according to the present invention is given by intensity. There are several ways of determining the diameter of the oil droplet size by intensity. Intensity is measured by use of a sizing instrument, suitably by dynamic light scattering such as the Malvern Zetasizer 4000 or suitably the Malvern Zetasizer 3000HS. A first possibility is to determine the z average diameter (ZAD) by dynamic light scattering (PCS, Photon correlation spectroscopy); this method additionally gives the polydispersity index (PDI), and both the ZAD and PDI are calculated with the cumulants algorithm. These values do not require the knowledge of the particle refractive index. A second mean is to calculate the diameter of the oil droplet by determining the whole particle size distribution by another algorithm, either the Contin, or non-negative least squares (NNLS), or the automatic "Malvern" one (the default algorithm provided for by the sizing instrument). Most of the time, as the particle refractive index of a complex composition is unknown, only the intensity distribution is taken into consideration, and if necessary the intensity means originating from this distribution.

Lipopolysaccharide (LPS) or lipooligosaccharide (LOS) derivatives or mutations or lipid A derivatives described herein are designed to be less toxic (e.g. 3D-MPL) than native lipopolysaccharides In one embodiment the adjuvant used for the compositions of the invention comprises an oil in water emulsion made from a metabolisable oil (such as squalene), an emulsifier (such as TWEEN 80) and optionally a tocol (such as alpha tocopherol). In one embodiment the adjuvant comprises (per 0.5 mL dose) 0.5-15, 1-13, 2-11, 4-8, or 5-6 mg (e.g. 2-3, 5-6, or 10-11 mg) metabolisable oil (such as squalene), 0.1-10, 0.3-8, 0.6-6, 0.9-5, 1-4, or 2-3 mg (e.g. 0.9-1.1, 2-3 or 4-5 mg) emulsifier (such as TWEEN 80) and optionally 0.5-20, 1-15, 2-12, 4-10, 5-7 mg (e.g. 11-13, 5-6, or 2-3 mg) tocol (such as alpha tocopherol).

The adjuvant may optionally further comprise 5-60, 10-50, or 20-30 μg (e.g. 5-15, 40-50, 10, 20, 30, 40 or 50 μg)lipid A derivative (for instance 3D-MPL).

The adjuvant may optionally contain 0.025-2.5, 0.05-1.5, 0.075-0.75, 0.1-0.3, or 0.125-0.25 mg (e.g. 0.2-0.3, 0.1-0.15, 0.25 or 0.125 mg) sterol (for instance cholesterol), 5-60, 10-50, or 20-30 μg (e.g. 5-15, 40-50, 10, 20, 30, 40 or 50 μg)lipid A derivative (for instance 3D-MPL), and 5-60, 10-50, or 20-30 μg (e.g. 5-15, 40-50, 10, 20, 30, 40 or 50 μg)saponin (for instance QS21).

In one embodiment, the adjuvant used for the compositions of the invention comprises aluminium phosphate and a lipid A derivative (such as 3D-MPL). This adjuvant may comprise (per 0.5 mL dose) 100-750, 200-500, or 300-400 μg Al as aluminium phosphate, and 5-60, 10-50, or 20-30 μg (e.g. 5-15, 40-50, 10, 20, 30, 40 or 50 μg)lipid A derivative (for instance 3D-MPL).

Method of Administration

The vaccine preparations containing immunogenic compositions of the present invention may be used to protect or treat a mammal susceptible to infection, by means of administering said vaccine via a systemic or mucosal route. These administrations may include injection via the intramuscular (IM), intraperitoneal (IP), intradermal (ID) or subcutaneous (SC) routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). For co-administration, the optional Th1 adjuvant may be present in any or all of the different administrations. In addition to a single route of administration, 2 different routes of administration may be used. For example, polysaccharide conjugates may be administered IM (or ID) and bacterial proteins may be administered IN (or ID). In addition, the vaccines of the invention may be administered IM for priming doses and IN for booster doses.

Following an initial vaccination, subjects may receive one or several booster immunizations adequately spaced.

Vaccine

The present invention further provides a vaccine containing the immunogenic compositions of the invention and a pharmaceutically acceptable excipient or carrier.

Pharmaceutically acceptable excipients and carriers are well known and can be selected by those of skill in the art. For example, the pharmaceutically acceptable excipient or carrier can include a buffer, such as Tris (trimethamine), phosphate (e.g. sodium phosphate), acetate, borate (e.g. sodium borate), citrate, glycine, histidine and succinate (e.g. sodium succinate), suitably sodium chloride, histidine, sodium phosphate or sodium succinate. The pharmaceutically acceptable excipient may include a salt, for example sodium chloride, potassium chloride or magnesium chloride. Optionally, the pharmaceutically acceptable excipient contains at least one component that stabilizes solubility and/or stability. Examples of solubilizing/stabilizing agents include detergents, for example laurel sarcosine and/or tween (e.g. TWEEN 80). Examples of stabilizing agents also include poloxamer (e.g. poloxamer 124, poloxamer 188, poloxamer 237, poloxamer 338 and poloxamer 407). The phamaceutically acceptable excipient may include a non-ionic surfactant, for example polyoxyethylene sorbitan fatty acid esters, Polysorbate-80 (TWEEN 80), Polysorbate-60 (TWEEN 60), Polysorbate-40 (TWEEN 40) and Polysorbate-20 (TWEEN 20), or polyoxyethylene alkyl ethers (suitably polysorbate-80). Alternative solubilizing/stabilizing agents include arginine, and glass forming polyols (such as sucrose, trehalose and the like). The pharmaceutically excipient may be a preservative, for example phenol, 2-phenoxyethanol, or thiomersal. Other pharmaceutically acceptable excipients include sugars (e.g. lactose, sucrose), and proteins (e.g. gelatine and albumin). Pharmaceutically acceptable carriers include water, saline solutions, aqueous dextrose and glycerol solutions. Numerous pharmaceutically acceptable excipients and carriers are known in the art and are described, e.g., in Remington's Pharmaceutical Sciences, by E. W. Martin, Mack Publishing Co., Easton, PA, 5th Edition (975).

According to a further aspect of the invention there is provided a process for making the immunogenic composition or vaccine of the invention comprising the step of mixing *S. pneumoniae* capsular polysaccharide (conjugates) of the invention, optionally with a pharmaceutically acceptable excipient or carrier.

Vaccine preparation is generally described in Vaccine Design ("The subunit and adjuvant approach" (eds Powell M. F. & Newman M. J.) (1995) Plenum Press New York).

Encapsulation within liposomes is described by Fullerton, U.S. Pat. No. 4,235,877.

The vaccines of the present invention may be stored in solution or lyophilized. In an embodiment, the solution is lyophilized in the presence of a sugar such as sucrose or lactose. It is still further preferable that they are lyophilized and extemporaneously reconstituted prior to use. Lyophilizing may result in a more stable composition (vaccine) and may possibly lead to higher antibody titers in the presence of 3D-MPL and in the absence of an aluminium based adjuvant.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms a preferred feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, US 5,704,911, U.S. Pat. Nos. 5,383,851, 5,893, 397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of the immunogenic composition in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are suitably present in as little as 0.1 to 10 μg, or 0.1 to 5 μg per dose; and the polysaccharide (suitably conjugated) antigens may be present in the range of 0.01-1 μg, and suitably between 0.01 to 0.5 μg of saccharide per dose.

As used herein, the term "intradermal delivery" means delivery of the vaccine or immunogenic composition to the region of the dermis in the skin. However, the vaccine or immunogenic composition will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine or immunogenic composition may ultimately be located solely or primarily within the dermis, or it may ultimately be distributed within the epidermis and the dermis.

The present invention further provides an improved vaccine for the prevention or amelioration of otitis media caused by *Haemophilus influenzae* by the addition of *Haemophilus influenzae* proteins, for example protein D in conjugated form. One or more *Moraxella catarrhalis* protein antigens can also be included in the vaccine or immunogenic composition of the invention in a free or conjugated form. Thus, the present invention is an improved method to elicit an immune response against otitis media in infants.

Examples of preferred *Moraxella catarrhalis* protein antigens which can be included in a combination vaccine or immunogenic composition of the invention (especially for the prevention of otitis media) are: outer membrane protein 106 (OMP106) [WO 97/41731 (Antex) & WO 96/34960 (PMC)]; outer membrane protein 21 (OMP21) or fragments thereof (WO 0018910); lactoferrin binding protein A (LbpA) &/or lactoferrin binding protein B (LbpB) [WO 98/55606 (PMC)]; transferrin binding protein A (TbpA) &/or transferring binding protein B (TbpB) [WO 97/13785 & WO 97/32980 (PMC)]; *Moraxella catarrhalis* CopB protein [Helminen M E, et al. (1993) Infect. Immun. 61:2003-2010]; ubiquitous surface protein A1 (UspA1) and/or ubiquitous surface protein A2 (UspA2) [WO 93/03761 (University of Texas)]; outer membrane protein CD (OmpCD); HasR (PCT/EP99/03824); PilQ (PCT/EP99/03823); outer membrane protein 85 (OMP85) (PCT/EP00/01468); lipo06 (GB 9917977.2); lipo10 (GB 9918208.1); lipo11 (GB 9918302.2); lipo18 (GB 9918038.2); outer membrane protein P6 (P6) (PCT/EP99/03038); D15 surface antigen (D15) (PCT/EP99/03822); outer membrane protein A1 (OmpA1) (PCT/EP99/06781); Hly3 (PCT/EP99/03257); and outer membrane protein E (OmpE). Examples of non-typeable *Haemophilus influenzae* proteins or fragments thereof which can be included in a combination vaccine (especially for the prevention of otitis media) include: Fimbrin protein [(U.S. Pat. No. 5,766,608—Ohio State Research Foundation)] and fusions comprising peptides therefrom [eg LB1(f) peptide fusions; U.S. Pat. No. 5,843,464 (OSU) or WO 99/64067]; outer membrane protein 26 (OMP26) [WO 97/01638 (Cortecs)]; P6 [EP 281673 (State University of New York)]; TbpA and/or TbpB; *H. influenzae* adhesin (Hia); *Haemophilus* surface fibrils (Hsf); *Haemophilus influenzae* Hin47 protein; *Haemophilus influenzae* Hif protein; *Haemophilus influenzae* Hmw1 protein; Haemophilus *influenzae* Hmw2 protein; *Haemophilus influenzae* Hmw3 protein; *Haemophilus influenzae* Hmw4 protein; *Haemophilus influenzae* autotransporter adhesin (Hap); D15 (WO 94/12641); P2; and P5 (WO 94/26304).

Methods of Treatment and Use

The present invention provides a method for the treatment or prevention of *Streptococcus pneumoniae* infection in a subject in need thereof comprising administering to said subject a therapeutically effective amount of an immunogenic composition or the vaccine of the invention. The present invention also provides a method of immunising a human host against *Streptococcus pneumoniae* infection comprising administering to the host an immunoprotective dose of the immunogenic composition or vaccine of the invention. The present invention also provides a method of inducing an immune response to *Streptococcus pneumoniae* (e.g. *Streptococcus pneumoniae* serotype 6A) in a subject, the method comprising administering a therapeutically effective amount of the immunogenic composition or vaccine of the invention.

In an embodiment, the present invention is an improved method to elicit an immune response in infants (defined as 0-2 years old in the context of the present invention) by administering a therapeutically effective amount of an immunogenic composition or vaccine of the invention. In one embodiment, the immune response is protective (i.e. it can prevent or reduce infection caused by *S. pneumoniae*). In one embodiment, the vaccine is a paediatric vaccine.

In an embodiment, the present invention is an improved method to elicit a (protective) immune response in the elderly population (in the context of the present invention a patient is considered elderly if they are 50 years or over in age, typically over 55 years and more generally over 60 years) by administering a therapeutically effective amount of the immunogenic composition or vaccine of the invention.

In one embodiment, the present invention provides a method of protecting a subject against a disease caused by infection with *Streptococcus pneumoniae*, or a method of preventing infection with *Streptococcus pneumoniae*, or a method of reducing the severity of or delaying the onset of at least one symptom associated with an infection caused by *Streptococcus pneumoniae*, the methods comprising administering to a subject an immunogenic amount of an immunogenic composition or vaccine of the invention.

In an embodiment, the present invention provides immunogenic compositions and vaccines of the invention for use in the prevention or treatment of a disease caused by *S. pneumoniae* infection. In an embodiment, the present invention provides the use of an immunogenic composition or vaccine of the invention in the manufacture of a medicament for the prevention (or treatment) of a disease caused by *S. pneumoniae* infection.

The disease caused by *Streptococcus pneumoniae* infection may be selected from pneumonia, invasive pneumococcal disease (IPD), exacerbations of chronic obstructive pulmonary disease (COPD), otitis media, meningitis, bacteraemia, pneumonia and/or conjunctivitis. Where the human host is an infant, the disease may be selected from otitis media, meningitis, bacteraemia, pneumonia and/or conjunctivitis. Where the human host is elderly, the disease may be selected from pneumonia, invasive pneumococcal disease (IPD), and/or exacerbations of chronic obstructive pulmonary disease (COPD).

Embodiments herein relating to "vaccine compositions" of the invention are also applicable to embodiments relating to "immunogenic compositions" of the invention, and vice versa.

Embodiments of the invention are further described in the subsequent numbered paragraphs:

Paragraph 1: A sized *Streptococcus pneumoniae* serotype 6A capsular polysaccharide wherein the average size ($M_w$) of the *Streptococcus pneumoniae* serotype 6A capsular polysaccharide is between 180-400, 210-400, 210-370, 220-360, 230-350, 240-340, 240-320, 240-310 or 250-310 kDa.

Paragraph 2: A sized *Streptococcus pneumoniae* serotype 6A capsular polysaccharide according to paragraph 1 which has been sized by a mechanical sizing technique.

Paragraph 3: A sized *Streptococcus pneumoniae* serotype 6A capsular polysaccharide according to paragraph 1 or paragraph 2 conjugated to a carrier protein (e.g. CRM-197).

Paragraph 4: A sized *Streptococcus pneumoniae* serotype 6A capsular polysaccharide according to paragraph 3 wherein the *Streptococcus pneumoniae* serotype 6A capsular polysaccharide is directly conjugated to the carrier protein.

Paragraph 5: A sized *Streptococcus pneumoniae* serotype 6A capsular polysaccharide according to any one of paragraphs 3-4 wherein the 6A polysaccharide is conjugated to the carrier protein or to a linker using CDAP chemistry.

Paragraph 6: A sized *Streptococcus pneumoniae* serotype 6A capsular polysaccharide according to any one of paragraphs 3-5 wherein the serotype 6A capsular polysaccharide (PS6A) is conjugated to the carrier protein or to a linker using CDAP chemistry using a CDAP:PS6A ratio between 1:2 to 3:1, 1:1.5 to 2:1, or 1:1.

Paragraph 7: A sized *Streptococcus pneumoniae* serotype 6A capsular polysaccharide according to any one of paragraphs 3-6 wherein the serotype 6A capsular polysaccharide is conjugated to the carrier protein or to a linker using CDAP chemistry wherein the reaction was carried out using a coupling time of between 50-130 minutes, 60-130 minutes, or 110-130 minutes.

Paragraph 8: A sized *Streptococcus pneumoniae* serotype 6A capsular polysaccharide according to any one of paragraphs 3-7 wherein the ratio of carrier protein to serotype 6A capsular polysaccharide is between 5:1 and 1:5, 4:1 and 1:1 or 2:1 and 1:1, 1.5:1 and 1:1, 1.4:1 and 1.3:1 (for example 1.2:1, 1.5:1) (w/w).

Paragraph 9: A sized *Streptococcus pneumoniae* serotype 6A capsular polysaccharide according to paragraphs 1-8 wherein the 6A capsular polysaccharide is sized by a factor of no more than x5.

Paragraph 10: A process for preparing a *Streptococcus pneumoniae* serotype 6A capsular polysaccharide conjugate comprising conjugating a sized *Streptococcus pneumoniae* serotype 6A capsular polysaccharide to a carrier protein or to a linker using CDAP chemistry using a CDAP:PS ratio between 1:2 to 3:1, 1:1.5 to 2:1, or 1:1.

Paragraph 11: A process according to paragraph 10 wherein the reaction was carried out using a coupling time of between 50-130 minutes, 60-130 minutes, or 110-130 minutes.

Paragraph 12: A process for preparing a *Streptococcus pneumoniae* serotype 6A capsular polysaccharide conjugate comprising (a) conjugation of a sized *Streptococcus pneumoniae* serotype 6A capsular polysaccharide to a carrier protein and (b) diafiltration against a solution having a concentration of NaCl below 150 mM.

Paragraph 13: An immunogenic composition comprising a sized *Streptococcus pneumoniae* serotype 6A capsular polysaccharide according to paragraphs 1-9 or *Streptococcus pneumoniae* serotype 6A capsular polysaccharide obtained by a process of any one of paragraphs 10-12 conjugated to a carrier protein.

Paragraph 14: An immunogenic composition according to paragraph 13 comprising 10 or more, 11 or more, 12 or more, 13 or more, 14 or more, 15 or more, or 16 or more capsular polysaccharides conjugates from different *S. pneumoniae* serotypes.

Paragraph 15: An immunogenic composition according to paragraph 13 or paragraph 14 comprising 1 or more, native capsular polysaccharides conjugates from *S. pneumoniae*.

Paragraph 16: An immunogenic composition according to paragraph 15 comprising native *Streptococcus pneumoniae* capsular serotype 6B polysaccharide.

Paragraph 17: An immunogenic composition according to paragraph 15 or 16 comprising native *Streptococcus pneumoniae* capsular serotype 23F polysaccharide.

Paragraph 18: An immunogenic composition according to any one of paragraphs 13 to 17 which comprises *Streptococcus pneumoniae* capsular serotype 6B polysaccharide having an average size ($M_w$) of between 500-1800, 900-1660, or 1000-1400 kDa.

Paragraph 19: An immunogenic composition according to any one of paragraphs 13 to 18 which comprises *Streptococcus pneumoniae* capsular serotype 23F polysaccharide having an average size ($M_w$) of between 500-1500, 600-1500, 700-1300, 900-1250, 800-1100, or 900-1000 kDa.

Paragraph 20: An immunogenic composition according to any one of paragraphs 13 to 19 which comprises *Streptococcus pneumoniae* capsular polysaccharide from: (a) serotype 1 having an average size ($M_w$) of between 100-1000, 200-800, 250-600, or 300-400 kDa; (b) serotype 4 having an average size ($M_w$) of between 50-500, 60-300, 70-150, or 75-125 kDa; (c) serotype 5 having an average size ($M_w$) of between 100-1000, 100-700, 100-350, or 150-300 kDa; (d) serotype 7F having an average size ($M_w$) of between 50-1000, 100-750, 150-500, or 200-300 kDa; (e) serotype 9V having an average size ($M_w$) of between 50-1000, 100-750, 150-500, 200-400, or 250-300 kDa; (f) serotype 14 having an average size ($M_w$) of between 50-1000, 100-750, 150-500, or 200-250 kDa; (g) 18C having an average size ($M_w$) of between 50-1000, 50-750, 50-500, 50-190, 50-150 or 80-110 kDa (h) serotype 19F having an average size ($M_w$) of between 50-1000, 100-750, 100-500, 100-190 or 120-180 kDa; and/or (i) serotype 19A having an average size ($M_w$) of between 50-800 kDa, 110-700, 110-300, 120-200, 130-180, 140-160 or 80-130 kDa.

Paragraph 21: An immunogenic composition according to any one of paragraphs 13 to 20 which further comprises *Streptococcus pneumoniae* capsular serotype 22F having an average size ($M_w$) of between 50 and 800 kDa, 110 and 700 kDa, 110-300, 120-200, 130-180, 150-170, 100-190, 100-150, 95-125 or 100-115 kDa.

Paragraph 22: An immunogenic composition according to any one of paragraphs 13 to 21 comprising 2, 3, 4, 5 or 6 different carrier proteins.

Paragraph 23: An immunogenic composition according to any one of paragraphs 13 to 22 wherein one or more or all carrier proteins is selected from the group consisting of: diphtheria toxoid (DT), CRM197, tetanus toxoid (TT), Fragment C of TT, dPly, PhtA, PhtB, PhtD, PhtE, PhtDE OmpC, PorB and *Haemophilus influenzae* Protein D.

Paragraph 24: An immunogenic composition of any one of paragraphs 13 to 23 wherein the *Streptococcus pneumoniae* capsular serotype 6B polysaccharide is conjugated to a different carrier protein (e.g. protein D) than the carrier protein to which *Streptococcus pneumoniae* serotype 6A capsular polysaccharide is conjugated.

Paragraph 25: An immunogenic composition of any one of paragraphs 13 to 24 comprising serotype 1 saccharide conjugated to protein D, serotype 4 saccharide conjugated to protein D, serotype 5 saccharide conjugated to protein D, serotype 6B saccharide conjugated to protein D, serotype 7F saccharide conjugated to protein D, serotype 9V saccharide conjugated to protein D, serotype 14 saccharide conjugated to protein D and serotype 23F saccharide conjugated to protein D.

Paragraph 26: An immunogenic composition according to any one of paragraphs 13 to 25 comprising serotype 19F conjugated to Diphtheria toxoid.

Paragraph 27: An immunogenic composition according to any one of paragraphs 13 to 26 wherein the composition comprises capsular saccharide 18C conjugated to tetanus toxoid (TT), optionally wherein 18C is the only saccharide in the composition conjugated to tetanus toxoid (TT), optionally via an ADH linker Paragraph 28: An immunogenic composition according to any of paragraphs 13 to 27 further comprising S. pneumoniae capsular saccharide(s) of one or more of: serotype 33F, serotype 15 and serotype 12F, conjugated to carrier protein(s).

Paragraph 29: An immunogenic composition according to any of paragraphs 13 to 28 wherein the dose of the 6A saccharide conjugate is between 1 and 10 µg, 1 and 5 µg, or 1 and 3 µg of saccharide (e.g. 2 µg).

Paragraph 30: An immunogenic composition according to any one of paragraphs 13 to 29 which further comprises one or more unconjugated or conjugated S pneumoniae proteins selected from: Poly Histidine Triad family (PhtX), Choline Binding Protein family (CbpX), CbpX truncates, LytX family, LytX truncates, CbpX truncate-LytX truncate chimeric proteins, detoxified pneumolysin (Ply), PspA, PsaA, Sp128, Sp101, Sp130, Sp125 and Sp133.

Paragraph 31: An immunogenic composition according to any one of paragraphs 13 to 30 which further comprises an adjuvant.

Paragraph 32: An immunogenic composition of paragraph 31 wherein the adjuvant comprises (per 0.5 mL dose) 100-750, 200-500, or 300-400 µg Al (aluminium) as aluminium phosphate.

Paragraph 33: A vaccine comprising the immunogenic composition of any one of paragraphs 13 to 32 and a pharmaceutically acceptable excipient or carrier.

Paragraph 34: A process for making the vaccine according to paragraph 33 which comprises the step of mixing the immunogenic composition of any of paragraphs 13 to 32 with a pharmaceutically acceptable excipient or carrier.

Paragraph 35: A method for the treatment or prevention of Streptococcus pneumoniae infection in a subject in need thereof comprising administering to said subject a therapeutically effective amount of an immunogenic composition of any of paragraphs 13 to 32 or the vaccine of paragraph 33.

Paragraph 36: A method of immunising a human host against Streptococcus pneumoniae infection comprising administering to the host an immunoprotective dose of the immunogenic composition of any of paragraphs 13 to 32 or vaccine of paragraph 34.

Paragraph 37: A method of inducing an immune response to Streptococcus pneumoniae serotype 6A in a subject, the method comprising administering a therapeutically or prophylactically effective amount of the immunogenic composition of any of paragraphs 13 to 32 or the vaccine of paragraph 33.

Paragraph 38: The immunogenic composition of paragraphs 13 to 32 or vaccine of paragraph 33 for use in the treatment or prevention of disease caused by Streptococcus pneumoniae infection.

Paragraph 39: A use of the immunogenic composition of paragraphs 12 to 32 or vaccine of paragraph 33 in the manufacture of a medicament for the treatment or prevention of a disease caused by Streptococcus pneumoniae infection.

All references or patent applications cited within this patent specification are incorporated by reference herein.

In order that this invention may be better understood, the following examples are set forth. These examples are for purposes of illustration only, and are not to be construed as limiting the scope of the invention in any manner.

Examples

Example 1—Preparation of Sized Polysaccharide

Sizing

A homogenizer EMULSIFLEX C-50 apparatus was used to reduce the molecular weight and the viscosity of the polysaccharide before the activation step (microfluidization). The efficiency of the sizing depended on the circuit pressure and on the total cycle's number. The homogenizing cell of EMULSIFLEX C-50 was replaced by a cell with a fixed geometry (Microfluidics F20Y-75 µm interaction chamber for E01 to E07; Microfluidics F30Y-125 µm interaction chamber for E08). The aim of the sizing was to reduce the molecular weight and the viscosity of the polysaccharide without a critical decrease of its antigenicity.

The size reduction was followed in-process by viscosimetry (Brookfield Programmable DV III+rheometer). When the target in viscosity was reached, the sized polysaccharide was characterized by HP-SEC-RI (high-performance size-exclusion chromatography, refractive index).

In-process characterizations of the $M_w$ were performed by HP-SEC-RI (TSK5000PW$_{XL}$ column+guard column). The elution was realised using a 50 mM Na/K$_2$PO$_4$, 500 mM NaCl pH 7.6 at a flow rate of 0.6 ml/min. The detection was realised by a refractive index detector. This characterization is based on the determination of a relative retention time (RRT). The RRT is calculated with regard to calibrated dextrans having a molecular weight in the linear range of separation of a TSK5000PW$_{XL}$ column. The RRT is defined by the following formula:

$$RRT = \frac{RT_{(sized\ PS)} - RT_{(HMW\ dext)}}{RT_{(LMW\ dext)} - RT_{(HMW\ dext)}}$$

$RT_{(sized\ PS)}$=retention time of sized PS (polysaccharide)
$RT_{(HMW\ dext)}$=retention time of high molecular weight dextran (dextran 1730 Kda)
$RT_{(LMW\ dext)}$=retention time of low molecular weight dextran (dextran 150 Kda)

The native serotype 6A polysaccharide was dissolved at 15 mg/ml during 4 hours in WFI (water for injection) at room temperature. After 4 hours of dissolution, the pH of the solution was adjusted at 6.5+/−0.5 before its transfer in a cold room to pursue dissolution overnight. Before the sizing, the solution of native serotype 6A polysaccharide was clarified on 5 µm filter.

The serotype 6A polysaccharide was then sized by Emulsiflex with a Microfluidics F30Y-125 µm homogenizing cell at a pressure of between 2900 and 3800. The sizing was stopped when the viscosity of the polysaccharide reached the targeted value for the viscosity (8.35 or 12.4). The number of cycles required depended on the target. For example, 32.5 cycles were needed to reach a viscosity of 12.4 cps using a pressure of 2900 psi. For this sample, in process determination of relative retention time by HP-SEC-RI gave a value of 0.28.

The sized 6A polysaccharide was filtered on a Millipak 20 (5 g scale) membrane (cut-off 0.22 µm) at a flow-rate of 10 ml/min.

The polysaccharide content of sized serotype 6A polysaccharide solution was accurately determined by colorimetric method (resorcinol) before its use in conjugation. Sized polysaccharide was characterized either by HP-SEC-MALLS or estimated by dextrans calibration curve and determination of antigenic activity (Table 1).

Antigenicity

Test and reference samples were incubated in microtiter plates previously coated with monoclonal antibodies raised against *S. pneumoniae* polysaccharide serotype 6A (PS6A). Rabbit polyclonal anti-PS6A antibodies were then added. Antigen-antibody complex were revealed using a goat anti-rabbit Ig peroxidase linked. Colour development was then performed by the system Ortho-phenylenediamine/$H_2O_2$ reacting with peroxidase. Coloration was measured by spectrophotometry (absorbances at 490 and 620 nm). The polysaccharide curve was compared to the reference curve (one native polysaccharide lot used as reference while another one native polysaccharide lot was used as internal control) in order to determine the polysaccharide concentration.

Measurement of Molecular weight and polydispersity by MALLS

The molecular weight ($M_w$) was determined by Laser Light Scattering (SEC-MALLS). In a first time, the analyses were performed on a TSK5000PWn (+guard column) using NaCl 0.2M+0.02% azide solution as elution buffer. Last analyses were performed on a TSKGMPW$_{XL}$ column (+guard column) with a loading of 100 µl of polysaccharide (1 mg/ml) using 50 mM Na/$K_2PO_4$, 200 mM NaCl pH 7.0 as elution buffer and a flow-rate of 0.75 ml/min.

The detection was realised with a laser spectrophotometer and an interferometric refractometer (Wyatt Otilab DSP equipped with a P100 cell and a red filter at 498 nm). The average molecular weight in number (Mr) was also obtained by MALLS. The polydispersity of the sized polysaccharide was obtained as the $M_w/M_n$ ratio. A theoretical do/dc of 0.14 was first used. When determined, the experimental value of 0.151 was used.

Example 2: Production of 6A Conjugates with Different Carriers a) Native *S. pneumoniae* serotype 6A polysaccharide vs. sized *S. pneumoniae* serotype 6A polysaccharide The activation and coupling conditions used to produce different 6A conjugates are given in Table 2.

TABLE 2

Specific activation/coupling/quenching conditions of *S. pneumoniae* serotype 6A polysaccharide - Protein D/PhtD conjugates

| Carrier | PD (lot PD003) (PS6A-PD conjugate) | PhtD (lot PhtD004) (PS6A-PhtD conjugate) | PhtD (lot PhtD008) (PS6A-PhtD conjugate) | dPly (lot dPly010) (PS6A-dPly conjugate) |
|---|---|---|---|---|
| PS6A conc. (mg/ml) | 5.5 | 5.5 | 10.0 | 10 |
| PS6A dissolution | Native PS NaCl 2M | Native PS NaCl 2M | Sized PS NaCl 2M | Sized PS NaCl 2M |
| Carrier protein concentration (mg/ml) | 5.0 | 10.0 | 20.0 | 10.0 |
| Initial Carrier protein/PS6A Ratio (w/w) | 1/1 | 3/1 | 3/1 | 3/1 |
| CDAP/PS6A ratio (mg/mg PS) | 0.75 | 1.5 | 1.5 | 1.5 |
| Coupling time pH$_c$/pH$_c$/pH$_q$ | 60 min 9.5/9.5/9.0 | 45 min 9.5/9.5/9.0 | 150 min 9.5/9.5/9.0 | 180 min 9.5/9.5/9.0 |

The final protein/PS6A ratio (w/w) for the resulting conjugates were:

PS6A-PD003: 0.6/1 (Native PS6A, $M_w$ by MALLS 1106 kDa)
PS6A-PhtD004: 1.4/1 (Native PS6A, $M_w$ by MALLS 1106 kDa)
PS6A-PhtD008: 2.7/1 (Sized PS6A, lot E01)
PS6A-dPly010: 1.65/1 (Sized PS6A, lot E01)

TABLE 1

Sized PS6A characterizations

| PS6A Lot | PS content (µg/ml) | RRT 150-1730 [1] | Viscosity (cp) | $M_W$ (kDa) [2] (estimation versus dextran calibration curve) | MALLS $M_W$ (kDa) $R_w$ (nm) Polydispersity | Antigenicity by ELISA (%) |
|---|---|---|---|---|---|---|
| E01 | 13650 | 0.45 | 8.35 | 575 | ND | 124 |
| E02 | 8570 | 0.50 | 6.03 | 514 | ND | ND |
| E03 | 14210 | 0.24 | 15.6 | 968 | ND | ND |
| E04 | 12000 | 0.21 | 17.3 | 1018 | | 120 [3] |
| E05 | — | — | — | — | — | — |
| E06 | 13910 | 0.24 | 12.1 | 916 | T13M/−70° C. 256 25.6 1.124 | 130 [3] |
| E07 | 14700 | 0.24 | 12.2 | 929 | 307.4 28.1 1.112 | 120 [3] |
| E08 | 13590 | 0.20 | 12.3 | 1004 | T12M/−70° C. 277 27.7 1.094 | 144 [3] |

[1] RRT: relative retention time (HP-SEC-RI)
[2] HP-SEC-RI
[3] relative value versus corresponding native polysaccharide. Remark: No MALLS values available at T0 for lots E06 and E08. Value at T13M (time = 13 minutes) or T12M (time = 12 minutes) could be considered as representative insofar as relative retention time and viscosity did not change between T0 (time = 0 minutes) and T13M or T12M for both samples.
ND means "not determined".

b) Sized polysaccharide conjugated to different carriers

The activation and coupling conditions used to produce different PS6A conjugates are given in Table 3.

TABLE 3

Specific activation/coupling/quenching conditions of PS6A-Protein D/CRM197/PhtD conjugates

| Carrier | PD (lot PDLS001 and lot PDLS002) (PS6A-PD conjugate) | CRM197 (lot CRM025) (PS6A-CRM197 conjugate) |
|---|---|---|
| PS6A conc. (mg/ml) | 10.0 | 10.0 |
| PS6A dissolution | NaCl 2M | NaCl 2M |
| Carrier protein concentration (mg/ml) | 10.0 | 10.0 |
| Initial Carrier protein/ PS6A Ratio (w/w) | 1.5/1 | 1.5/1 |
| CDAP conc. (mg/mg PS) | 1.5 | 1 |
| Coupling time | 120 min | 120 min |
| $pH_a/pH_c/pH_q$ | 9.5/9.5/9.0 | 9.5/9.5/9.0 |

The final protein/PS6A ratio (w/w) for the resulting conjugates were:

PS6A-PD/LS001 and PS6A-PD/LS002: 1.6/1 (Sized PS6A, lot E06)

PS6A-CRM197/025: 1.3/1 (Sized PS6A, lot E03)

PS6AAH-PhtD Conjugate (Lot 6A-PhtD106)

In a second conjugation method PS6A was linked to the carrier protein PhtD via a linker—Adipic acid dihydrazide (ADH); this conjugate is designated PS6AAH-PhtD.

PS6A derivatization

Activation and coupling were performed at 25° C. under continuous stirring in a temperature-controlled waterbath. Microfluidized PS6A was diluted to obtain a final polysaccharide concentration of 10 mg/ml in water for injection (WFI) and the solution was adjusted at pH 6.0±0.2 with 0.1N HCl. CDAP solution (100 mg/ml freshly prepared in acetonitrile/WFI, 50/50) was added to reach the appropriate CDAP/PS ratio (1/1, w/w).

The pH was raised up to the activation pH 9.00±0.05 by the addition of 0.2M NaOH. After 3 minutes, ADH was added to reach the appropriate ADH/PS ratio (8.9/1 w/w); the pH was regulated to coupling pH 9.0. The solution was left for 1 hour under pH regulation. The $PS_{AH}$ derivative was then dialysed against 0.2M NaCl.

Coupling

PhtD at 7.5 mg/ml in 0.2M NaCl was added to the PS6AAH derivative (PS6A with the ADH linker) in order to reach a PhtD/PS6AAH ratio of 3/1 (w/w). The pH was adjusted to 5.0±0.05 with HCl. The EDAC solution (50 mg/ml in 0.1M Tris-HCl pH 7.5) was added manually in 10 min (20 µl/min) to reach 0.5 mg EDAC/mg PS6AAH. The resulting solution was incubated for 45 min at room temperature under stirring and pH regulation. The solution was neutralized by addition of 1 ml of 1M Tris-HCl pH 7.5 and let 30 min at room temperature.

Prior to the elution on SEPHACRYL S400HR, the conjugate was clarified using a 5 pm Minisart filter. The resulting conjugate PS6AAH-PhtD106 had a final PhtD/PS6A ratio of 2.84 (w/w).

A target in relative retention time was chosen (RRT 150-1730 around 0.50). Several conjugates (6A-PhtD004 (native polysaccharide) and 6A-PhtD008 (sized polysaccharide) (as described above) were produced with sized polysaccharide and were compared to conjugates produced with native PS6A.

Example 3: Preclinical Evaluation of Anti-PS6A Responses

Groups of 40 mice were immunized IM at days 0, 14 and 28 with 14 valent (14V) formulations containing PS6A conjugates (at 1/10 of human dose) using AlPO4 as adjuvant. Anti-PS6A ELISA IgG titers and Opsonophagocytosis (OP) titers were measured in individual sera collected at day 42.

The 14V-formulation contained the following conjugates: 1-PD, 3-PD, 4-PD, 5-PD, 6B-PD, 7F-PD, 9V-PD, 14-PD, 18C-$TT_{AH}$, 19A-dPly, 19F-DT, 22F-PhtD, 23F-PD. The serotype 6A was conjugated with PD, PhtD or dPly as carrier.

Results are summarized in FIG. 1 ELISA anti-PS6A response.

Conclusions

The highest anti-PS6A ELISA IgG titers were obtained with the PS6A-PD conjugate produced with a native polysaccharide (1106 kDa). The evaluation showed a trend to a lower immunogenicity for conjugates with sized polysaccharide. Using PhtD as carrier, a lower anti-PS ELISA IgG titer was observed with the conjugate produced with a sized polysaccharide (14V (6A-PhtD/008 using lot E01). Subsequently, as described in the following examples, a change in sizing target was investigated to produce a PS6A with robustness of process and immunogenicity of resulting conjugates. The following experiments were carried out to evaluate sized polysaccharide having a higher molecular weight than PS6A from lot E01.

Example 4: Evaluation of Sized PS6A-CRM197 Conjugates

For each conjugate, conjugation parameters are given in Table 4 (PS6A and carrier concentrations, initial carrier/PS6A ratio(w/w), coupling time and CDAP/PS6A ratio (w/w)

Preparation of the solutions

CDAP solution

Just before activation, a cyanodiaminopyridinium tetrafluoroborate (CDAP) solution was prepared at 100 mg/ml in acetonitrile/water for injection (50/50 (v/v))

Activation

Native or sized PS6A was diluted at a defined concentration and the pH of the solution was set to 6.0±0.2. At time 0, the CDAP solution was added manually in order to obtain a defined CDAP/PS6A ratio (w/w).

After 1.5 minutes the pH was raised up to activation pH value by addition of NaOH. At time 4.5 minutes, the protein solution (at a defined concentration and buffer) was added in order to obtain a fixed protein/PS6A ratio (w/w). The pH of the solution was regulated at coupling pH value during a defined timing (coupling time—See Table 4).

At time T=coupling time+4 min 30, a solution of Glycine 2M pH 9.0 was added to quench the reaction. After 30 minutes of quenching, the conjugate was directly injected on purification column or let overnight under continuous stirring at +2 to+8° C. before purification.

Purification

Before purification, the conjugate solution was filtered through a 5 µm or 10 µm membrane in order to remove aggregates and particles. Conjugate was then purified on SEPHACRYL S400HR column (bed height: 100 cm+/−10 cm) using NaCl 150 mM as eluent. The conjugate was then sterile filtered on 0.22 µm PVDF (polyvinylidene difluoride) membrane. The sterilised bulk (Conjugated Bulk) was stored at +2-8° C. until formulation.

Characterization

The final Protein/Polysaccharide ratio (w/w) on the sterilized conjugate was determined by the ratio of the Lowry/resorcinol concentrations. Antigenicity and free PS (polysaccharide) content were determined using methods described here below. Data are shown in Table 5.

Antigenicity Test

Native polysaccharide was assigned an antigenicity index value of 100%. Insofar as correlation between antigenicity index and immunogenicity had not been established, the determination of sized polysaccharide antigenicity was performed as indicative value. The objective was to keep this value as high as possible. This value was determined by ELISA.

The antigenicity of polysaccharide was determined in a sandwich-type ELISA (see Example 1 for measurement of antigenicity).

Free PS Content by ELISA

After reaction of the conjugate with anti-carrier serum, the complex was precipitated using saturated ammonium sulphate (SAS). After centrifugation, the free PS06A content was performed by ELISA (anti-PS/anti-PS, see part 2.8.1.2) on the supernatant. The percentage of free PS was calculated proportionally to the total PS content measured by resorcinol method.

The absence of conjugate in the supernatant was also controlled by a α-carrier/α-PS06A ELISA.

TABLE 4

Process conditions for PS6A-CRM197 conjugates at 50 mg scale

| Conjugate | PS6A | PS Dissolution (M NaCl) | [mg/ml] | Carrier Dissolution buffer | [mg/ml] |
|---|---|---|---|---|---|
| PS6A-CRM197/015 | native | 2 | 5 | K/K$_2$PO$_4$ 10 mM pH7 2NaCl 0.2M | 10 |
| PS6A-CRM197/016 | native | 2 | 5 | K/K$_2$PO$_4$ 10 mM pH7 2NaCl 0.2M | 10 |
| PS6A-CRM197/017 | E01 | 2 | 10 | K/K$_2$PO$_4$ 10 mM pH7 2NaCl 0.2M | 10 |
| PS6A-CRM197/018 | E01 | 2 | 10 | K/K$_2$PO$_4$ 10 mM pH7 2NaCl 0.2M | 10 |
| PS6A-CRM197/019 | E01 | 2 | 10 | K/K$_2$PO$_4$ 10 mM pH7 2NaCl 0.2M | 10 |
| PS6A-CRM197/020 | E01 | 2 | 10 | K/K$_2$PO$_4$ 10 mM pH7 2NaCl 0.2M | 10 |
| PS6A-CRM197/021 | E01 | 2 | 10 | K/K$_2$PO$_4$ 10 mM pH7 2NaCl 0.2M | 10 |
| PS6A-CRM197/022 | E03 | 2 | 10 | K/K$_2$PO$_4$ 10 mM pH7 2NaCl 0.2M | 10 |
| PS6A-CRM197/023 | E03 | 2 | 10 | K/K$_2$PO$_4$ 10 mM pH7 2NaCl 0.2M | 10 |
| PS6A-CRM197/024 | E03 | 2 | 10 | K/K$_2$PO$_4$ 10 mM pH7 2NaCl 0.2M | 10 |

| Conjugate | Initial Ratio (w/w) | CDAP (mg/mg PS) | Coupling Time (min) | pHa/pHc/PHq | Remark |
|---|---|---|---|---|---|
| PS6A-CRM197/015 | 1.5/1 | 1.5/1 | 60 | 9.5/9.5/9.0 | 50 mg |
| PS6A-CRM197/016 | 1.5/1 | 0.75/1 | 60 | 9.5/9.5/9 | 50 mg |
| PS6A-CRM197/017 | 1.5/1 | 0.75/1 | 120 | 9.5/9.5/9 | 50 mg |
| PS6A-CRM197/018 | 1.5/1 | 1.5/1 | 120 | 9.5/9.5/9 | 50 mg |
| PS6A-CRM197/019 | 1.5/1 | 1/1 | 120 | 9.5/9.5/9 | 50 mg |
| PS6A-CRM197/020 | 2/1 | 0.75/1 | 120 | 9.5/9.5/9 | 50 mg |
| PS6A-CRM197/021 | 1.5/1 | 1.5/1 | 120 | 9.5/9.5/9 | 200 mg |

TABLE 4-continued

Process conditions for PS6A-CRM197 conjugates at 50 mg scale

| | | | | | |
|---|---|---|---|---|---|
| PS6A-CRM197/022 | 1.5/1 | 1.5/1 | 120 | 9.5/9.5/9 | 50 mg |
| PS6A-CRM197/023 | 1.5/1 | 1.5/1 | 60 | 9.5/9.5/9 | 50 mg |
| PS6A-CRM197/024 | 1.5/1 | 1/1 | 120 | 9.5/9.5/9 | 50 mg |

Note:
Designation such as "PS6ACRM197/024" indicates PS6ACRM197 from lot024.

TABLE 5

Characterization of PS6A-CRM197 conjugates at 50 mg-PS scale

| Conjugate | Final Ratio Carrier/PS (w/w) | Free polysaccharide ELISA (%) 4° C. | αPS/αPS (%) 4° C. | αprot/αPS (%) 4° C. | Yield (%) | Remark |
|---|---|---|---|---|---|---|
| PS6A-CRM197/015 | 0.91/1 | | | | 58.8 | Filtration issue |
| PS6A-CRM197/016 | 0.65/1 | | | | 45.1 | |
| PS6A-CRM197/017 | 1.23/1 | | | | 28.2 | Tightened pool/bad separation |
| PS6A-CRM197/018 | 1.33/1 (NF) | | | | 48.3 | |
| PS6A-CRM197/019 | 1.10/1 | | | | 50.2 | |
| PS6A-CRM197/020 | 1.41/1 | | | | 50.6 | |
| PS6A-CRM197/021 | 1.42/1 | 0.8 | 35 | 125 | 45.4 | |
| PS6A-CRM197/022 | 1.11/1 | 1.1 | 23 | 67 | 69.8 | Filtration issue |
| PS6A-CRM197/023 | 1.24/1 | 0.8 | 27 | 98 | 61.4 | |
| PS6A-CRM197/024 | 1.19/1 | 1.3 | 31 | 95 | 65.3 | |

The first set of conjugates (PS6A-CRM197/015, PS6A-CRM197/016) were produced with native polysaccharide ($M_w$ by MALLS 990 kDa) and showed limitations in term of reachable final CRM/PS ratio and filterability of resulting conjugates (Table 5).

A second set of conjugates (PS6A-CRM197/017, PS6A-CRM197/018, PS6A-CRM197/019, PS6A-CRM197/020, PS6A-CRM197/021) were produced using sized polysaccharide (lot E01). By increasing CDAP/PS ratio and/or initial CRM/PS ratio, the desired final CRM/PS ratio and polysaccharide yield could be reached. The best conditions (PS6A-CRM197/021) were reproduced with a new sized polysaccharide lots but having a higher molecular weight (lot E03) than the previous one. However a filtration issue was observed. It was found that by reducing coupling time or CDAP/PS6A ratio, the filtration issue was solved.

A third set of conjugates (PS6A-CRM197/022, PS6A-CRM197/023, PS6A-CRM197/024) were produced using sized serotype 6A polysaccharide (lot E03). The best conditions (PS6A-CRM197/024) were the following: a polysaccharide concentration of 10 mg/ml in 2M NaCl, a CDAP/PS ratio of 1/1 (w/w), a CRM concentration of 10 mg/ml in 10 mM K/K$_2$ PO$_4$ pH 7.2, 0.2M NaCl, an initial CRM/PS ratio of 1.5/1 (w/w), a pH for activation and coupling of 9.5 and a coupling time of 120 min. Resulting conjugates had a final CRM/PS ratio around 1.2/1 (w/w) for a global yield around 65%.

Example 5: Production of Sized 6A-CRM197 Conjugates at 200 Mg Scale

A scale up at 200 mg-PS scale was performed (Table 6 and Table 7).

TABLE 6

Process conditions for PS6A-CRM197 conjugates at 200 mg-PS scale

| Conjugate | Lot | Estimated molecular weight (kDa)* | PS Dissolution (M NaCl) | [mg/ml] | Lot | Carrier Dissolution buffer | [mg/ml] |
|---|---|---|---|---|---|---|---|
| PS6A-CRM197/025 | E03 | 968 | 2 | 10 | CRM197-012 | K/K$_2$PO$_4$ 10 mM pH 7 2 NaCl 0.2 M | 10 |
| PS6A-CRM197/026 | E03 | 968 | 2 | 10 | CRM197-012 | K/K$_2$PO$_4$ 10 mM pH 7 2 NaCl 0.2 M | 10 |

TABLE 6-continued

| | | | | | | | |
|---|---|---|---|---|---|---|---|
| PS6A-CRM197/027 | E03 | 968 | 2 | 10 | CRM197-009 | K/K$_2$PO$_4$ 10 mM pH 7 2 NaCl 0.2 M | 10 |
| PS6A-CRM197/028 | E07 | 929 | 2 | 10 | CRM197-014 | K/K$_2$PO$_4$ 10 mM pH 7 2 NaCl 2 M | 10 |
| PS6A-CRM197/029 | E07 | 929 | 2 | 10 | CRM197-014 | K/K$_2$PO$_4$ 10 mM pH 7 2 NaCl 0.2 M | 10 |
| PS6A-CRM197/030 | E08 | 1004 | 2 | 10 | CRM197-014 | K/K$_2$PO$_4$ 10 mM pH 7 2 NaCl 2 M | 10 |

*Estimation realized using a dextran calibration curve (see Table 1 for MALLS data)

| Conjugate | Initial Ratio (w/w) | CDAP (mg/mg PS) | CouplingTime (min) | pHa/pHc/pHq |
|---|---|---|---|---|
| PS6A-CRM197/025 | 1.5/1 | 1/1 | 120 | 9.5/9.5/9 |
| PS6A-CRM197/026 | 1.5/1 | 1/1 | 120 | 9.5/9.5/9 |
| PS6A-CRM197/027 | 1.5/1 | 1/1 | 120 | 9.5/9.5/9 |
| PS6A-CRM197/028 | 1.5/1 | 1/1 | 120 | 9.5/9.5/9 |
| PS6A-CRM197/029 | 1.5/1 | 1/1 | 120 | 9.5/9.5/9 |
| PS6A-CRM197/030 | 1.5/1 | 1/1 | 120 | 9.5/9.5/9 |

TABLE 7

Characterization of PS6A-CRM conjugates at 200 mg-PS scale

| Conjugate | F. Ratio Carrier/PS (w/w) | Free PS ELISA (%) 4° C. | αPS/αPS (%) 4° C. | αprot/αPS (%) 4° C. | Yield (%) |
|---|---|---|---|---|---|
| PS6A-CRM197/025 | 1.32/1 | 0.2 | 56 | 132 | 56.6 |
| PS6A-CRM197/026 | 1.20/1 | 0.1 | 50 | 125 | 56.2 |
| PS6A-CRM197/027 | 1.25/1 | 0.2 | 49 | 113 | 57.6 |
| PS6A-CRM197/028 | 1.18/1 | | 44 | 89 | 60.2 |
| PS6A-CRM197/029 | 1.22/1 | | 36 | 101 | 67.8 |
| PS6A-CRM197/030 | 1.36/1 | | 28 | 91 | 56.4 |
| Remark | | E6A-417 | PS6A-CRM197/025 | | |

Data from 200 mg-PS scale lots was consistent with data obtained at small scale. Resulting conjugates had final CRM/PS ratio between 1.25 to 1.32/1, for a global polysaccharide yield of 56%. In term of stability, no issue appeared in HP-SEC analyses or free polysaccharide content by ELISA (data not available with chemical method).

Based on these results, further lots (see Table 5 below) were produced in the following conditions: a polysaccharide concentration of 10 mg/ml in 2M NaCl, a CDAP/PS ratio of 1/1 (w/w), a CRM concentration of 10 mg/ml in 10 mM K/K$_2$PO$_4$ pH 7.2, 2M NaCl, an initial CRM/PS ratio of 1.5/1 (w/w), a pH for activation and coupling of 9.5 and a coupling time of 120 min.

Example 6: Immunogenicity of PS6A Conjugates in Mice

Different sized PS6A conjugates were evaluated in Balb/c mice (as monovalent formulation): 6A-CRM197 (PS6A-CRM025), 6A-PD (PS6A-PDLS001(E06)), 6A-PD (PS6A-PDLS002(E06)), 6A-PhtD (PS6A-PhtD008) and 6AAH-PhtD (PS6A-PhtD106 (E04)), PS6A-PhtD (PS6A-PhtD100 (E06)) conjugates produced with a sized PS.

Figure 2:
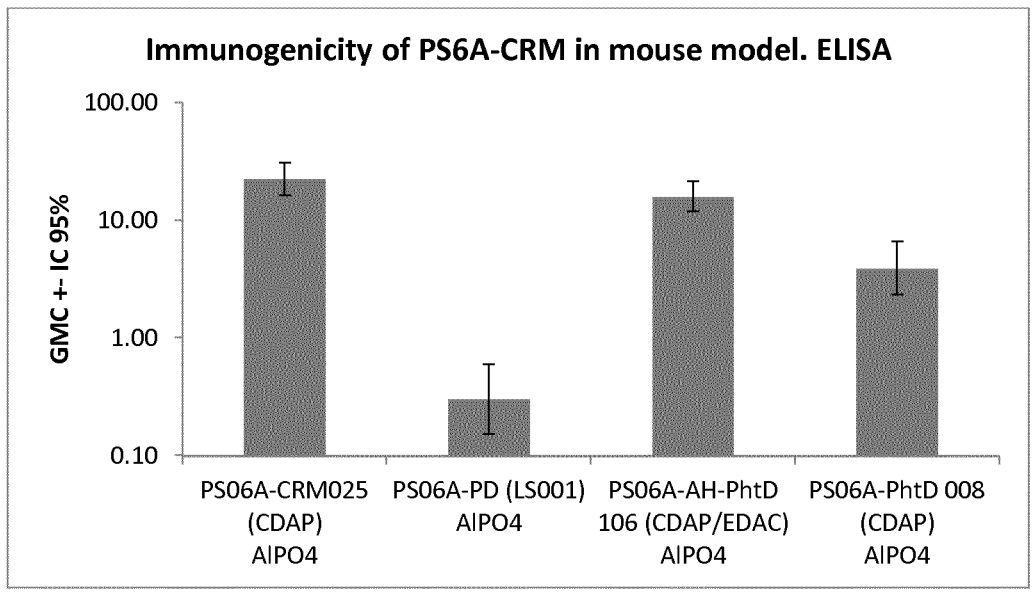
FIG. 2(A) Immunogenicity of PS6A-CRM197 in the Balb/c mouse model ELISA results
FIG. 2(B) Immunogenicity of PS6A-CRM197 in the Balb/c mouse model OPA results
Figure 2:
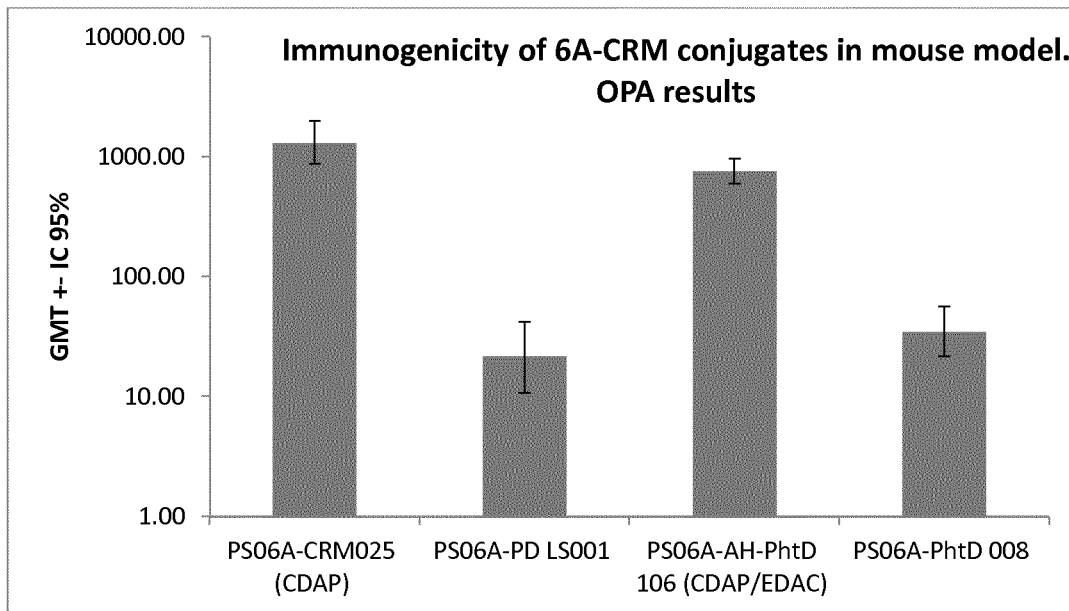

34 Balb/c Mice were immunized three times (days 0-14-28) with 0.3 μg of different PS6A conjugates adsorbed onto AlPO4. Anti-PS6A ELISA IgG titers levels and Opsonophagocytosis (OP) titers were measured in individual sera collected at day 42. Results are shown in FIGS. 2A and 2B. A significantly higher antibody response was induced by PS6A-AH-PhtD (CDAP/EDAC) and PS6A-CRM 025 (CDAP) in ELISA and OPA.

Example 7: Characterisation of Sized PS6A

CRM197 Concentration

Thawing of CRM197 Purified bulk is stored at −20° C. at a concentration of 1.917 mg/ml in 10 mM K/K$_2$PO$_4$ pH 7.2. 7.5 g of purified bulk were thawed overnight at +2/+8° C.

Concentration by UF

The ultrafiltration was realized at room temperature on a centramate device.

The ultrafiltration membrane was an OMEGA medium screen membrane of 0.09 m$^2$ with a 10 kDa cut off (2 membranes). The circulation flow-rate was 1200 ml/min and the transmembrane pressure applied during the run was between 7-10 psi.

The CRM197 bulk was 7.5-fold concentrated in order to reach a concentration of around 15 mg/ml (target for conjugation>10 mg/ml).

Filtration on 0.22 μm

After the ultrafiltration, the concentrated bulk was sterile filtered on 0.22 μm Millipack 20 filter (PVDF) at 20 ml/min. It was then stored at −20° C. until its use in coupling.

The sized PS6A was characterized by the following test: MALLS and antigen content by ELISA. Stability was evaluated following 2 months at −70° C. (T=0 compared to T=2 months). No stability issue observed when the sized PS6A is stored at −70° C. Results of sized PS6A characterization are summarized in (Table 8).

TABLE 8

Characterization data and stability of sized PS6A

| | T = 0 | T = 2M at −70° C. |
|---|---|---|
| Antigen content by resorcinol (IP value) | 15487 μg/ml | / |
| Mean molecular weight in weight by MALLS | 302.1 kDa | 288.8 kDa |
| Root mean square radius in weight by MALLS | 27.7 nm | 27.3 nm |

TABLE 8-continued

Characterization data and stability of sized PS6A

|  | T = 0 | T = 2M at −70° C. |
|---|---|---|
| Polydispersity ratio (M$_w$/Mn) by MALLS | 1.102 | 1.136 |
| Antigen content by ELISA | 22250 μg/ml | 22911 μg/ml |
| Ratio ELISA/resorcinol (%) | 144% | 148% |

Two conjugates (DO6ADJA001, DO6ADJA002) were produced at 2g-PS scale using lot of sized PS6A and lot as carrier. The conditions of conjugation are described hereafter.

The reaction was performed at 25+/−1° C. in a 1L-bioreactor.

2 g of sized PS6A was diluted at 10 mg/ml in 2M NaCl and the pH of the solution was adjusted at 6.0+/−0.2 with 0.05N HCl solution.

At T=0, 2 g of CDAP in solution (solution at 100 mg/ml in CH$_3$CN/H$_2$O 50/50) was manually added to the solution (CDAP/PS ratio=1.0/1 w/w).

At T=1 min 30, pH was increased up to 9.5+1-0.05 by addition of 0.5N NaOH. It took approximately 90 sec to reach the target pH.

At T=4 min 30, 3 g of CRM197 (solution at 10 mg/ml in 10 mM KH$_2$PO$_4$/K$_2$HPO$_4$ pH 7.2, 2M NaCl) was added at the solution of activated PS6A in 1 minute in order to reach a CRM197/PS6A ratio of 1.5/1 w/w. The pH was regulated at 9.5+/−0.05 during 120 minutes. At T=124 min 30, 100 ml of a solution of 2M glycine pH 9.0 was added to quench the conjugate (Ratio Gly/PS=7.5/1 w/w). After 30 minutes of quenching, the pH of the mixture was adjusted to 6.5+/−0.2 using 5N HCl. When pH was stabilized, the conjugate was let overnight under continuous stirring at +2/+8° C. before clarification and purification.

Purification

Prior to the elution on SEPHACRYL S400HR, the conjugate was clarified using a 10 pm Kleenpack HDCII filter at 50 ml/min The conjugate was then injected on a SEPHACRYL S400HR. Elution was done with 0.15M NaCl solution and the collection pool was based on a Kd value. Kd is the distribution coefficient (Kd=(V$_e$−V$_0$)/(V$_t$−V) V$_e$=elution volume, V$_0$=void volume, V$_t$=total volume of the column.

The following criteria were used for the pool collection: from OD$_{280\ nm}$=0.05 AU to a Kd value of 0.28.

Sterilizing Filtration

Before filtration, the bulk was brought back to room temperature.

Lots were filtered on Opticap 4" sterilizing membrane (1900 cm$^2$, PVDF) at a flow-rate of 40 ml/min. The filter was rinsed by 0.15M NaCl buffer before filtration. After filtration, 200 ml of 0.15M NaCl was passed through filter to limit the loss of material. No issue appeared during filtration.

Preclinical Evaluation

Groups of 48 female Balb/c mice (4-weeks-old) were immunized IM at days 0,14 and 28 with adsorbed conjugates formulations (AlPO$_4$) containing 0.1 μg of either DO6ADJA001, DO6ADJA002, PS6A-CRMLS001 (produced with sized PS6A, lot E07), PS6A-CRMLS002 (produced with sized PS6A, lot E07) or PS6A-PDLS001 (as a benchmark).

Figure 3A:
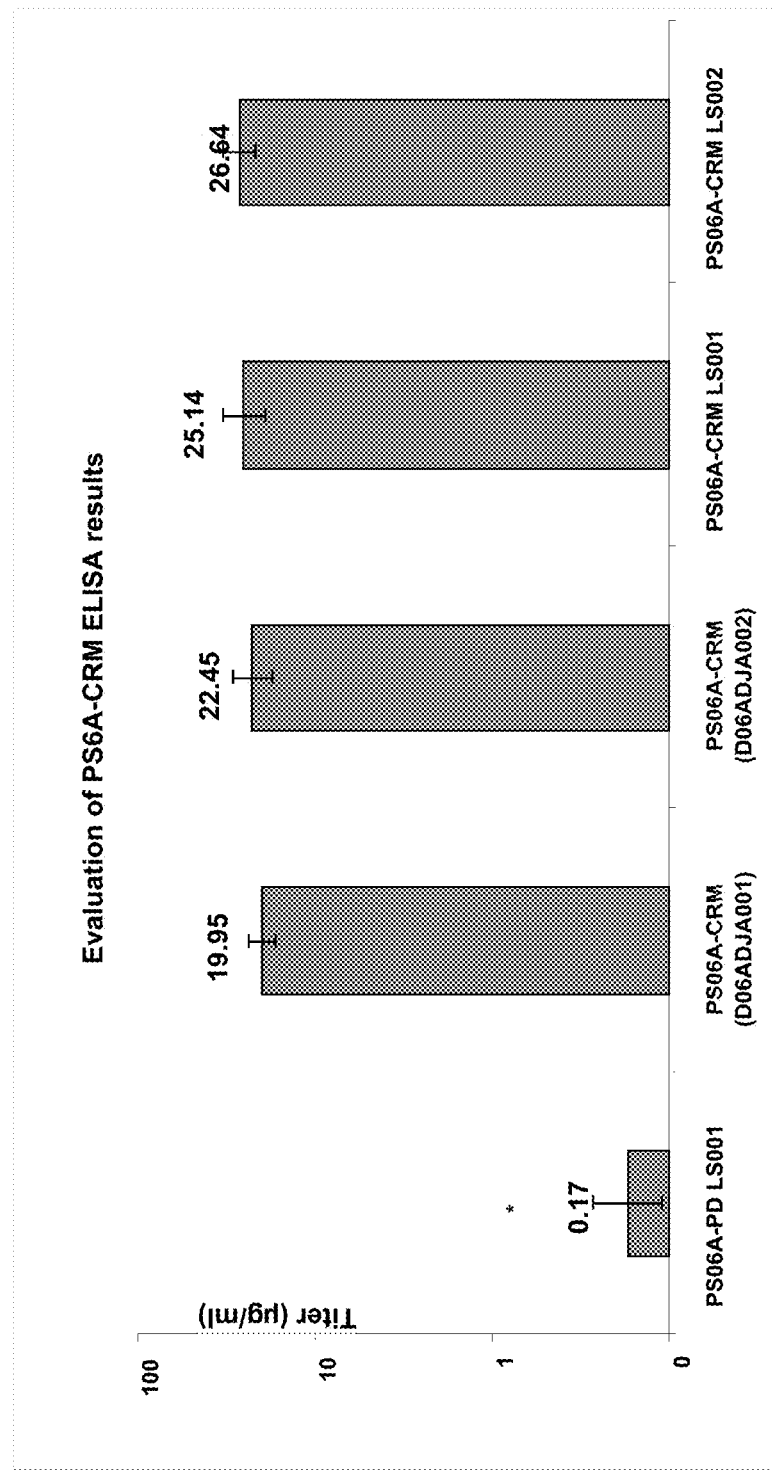
FIG. 3(A) Evaluation of PS6A-CRM197 ELISA results
Figure 3B:
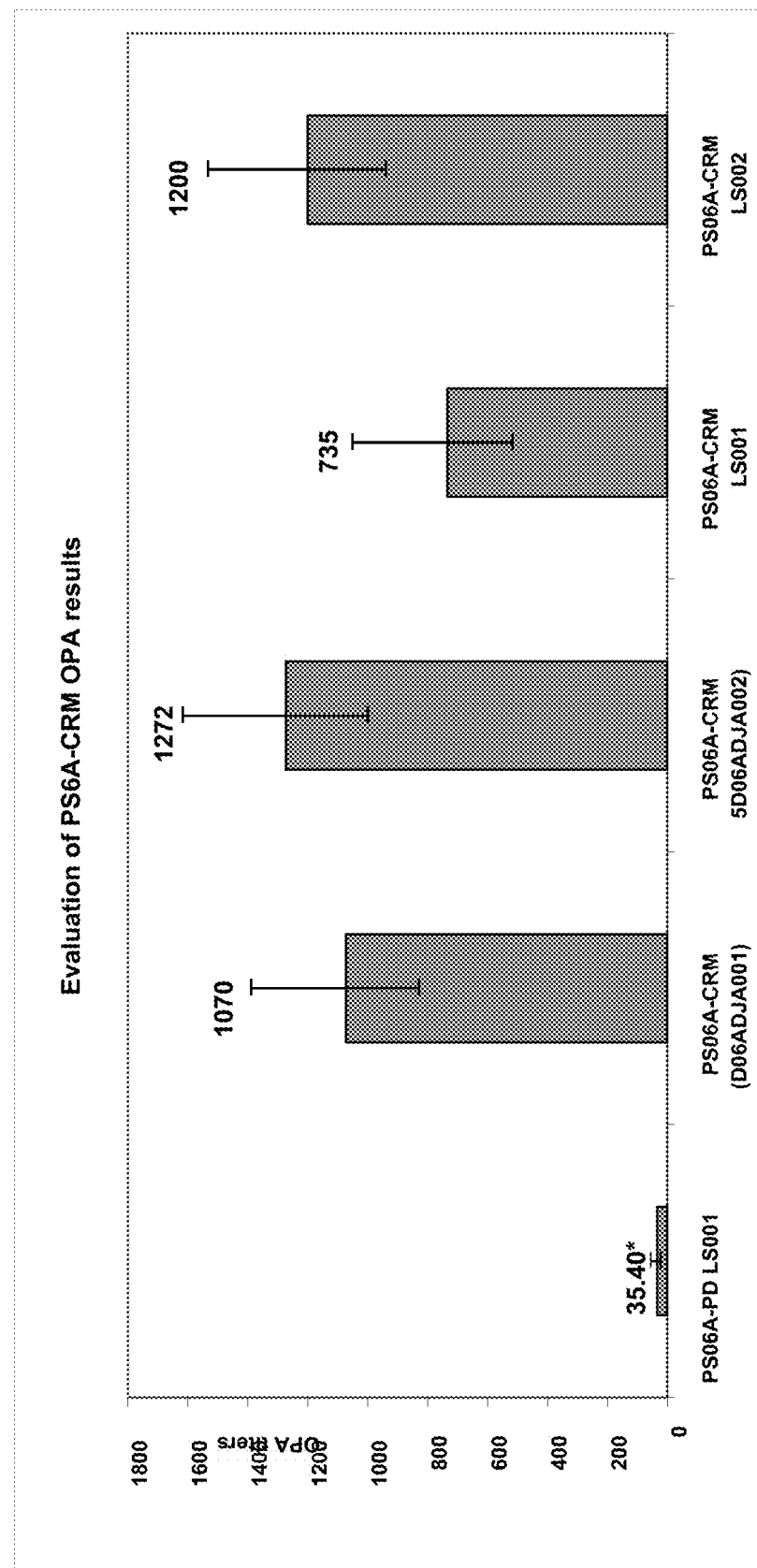
FIG. 3(B) Evaluation of PS6A-CRM197 OPA results

Anti-PS6A IgG levels (FIG. 3A) and opsono-phagocytosis titers (FIG. 3B) were measured in individual sera collected at day 42. No significant difference was observed in antibody responses induced by the PS6A-CRM produced according to Example 7 compared to the PS6A-CRM produced according to Example 5 in ELISA and in OPA.

Example 8: Preparation of 6A Conjugate

Sized 6A conjugate (lot E06AADJA059) was produced at 15 g PS scale in a 15 L reactor using the conjugation parameters of the sized 6A produced at 200 mg PS scale (see Example 5). Conjugate was then purified on SEPHACRYL S400HR column (BPG450 column (GE Healthcare)) using NaCl 150 mM as eluent. The conjugate was then sterile filtered on 0.22 m PDVF membrane and stored at 2-8° C. The conjugate was concentrated (5×) and diafiltrated (10 diafiltration volume) against WFI (water for injection) using a 10 kDa MWCO OMEGA PES membrane (T-series, PALL). The retentate was then filtered on 0.22 μm membrane.

```
SEQ ID NO: 1:
MetLysLeuLysThrLeuAlaLeuSerLeuLeuAlaAlaGlyValLeu

AlaGlyCysSerSerHisSerSerAsnMetAlaAsnThrGlnMetLys

SerAspLysIleIleIleAlaHisArgGlyAlaSerGlyTyrLeuPro

GluHisThrLeuGluSerLysAlaLeuAlaPheAlaGlnGlnAlaAsp

TyrLeuGluGlnAspLeuAlaMetThrLysAspGlyArgLeuValVal

IleHisAspHisPheLeuAspGlyLeuThrAspValAlaLysLysPhe

ProHisArgHisArgLysAspGlyArgTyrTyrValIleAspPheThr

LeuLysGluIleGlnSerLeuGluMetThrGluAsnPheGluThrLys

AspGlyLysGlnAlaGlnValTyrProAsnArgPheProLeuTrpLys

SerHisPheArgIleHisThrPheGluAspGluIleGluPheIleGln

GlyLeuGluLysSerThrGlyLysLysValGlyIleTyrProGluIle

LysAlaProTrpPheHisHisGlnAsnGlyLysAspIleAlaAlaGlu

ThrLeuLysValLeuLysLysTyrGlyTyrAspLysLysThrAspMet

ValTyrLeuGlnThrPheAspPheAsnGluLeuLysArgIleLysThr

GluLeuLeuProGlnMetGlyMetAspLeuLysLeuValGlnLeuIle

AlaTyrThrAspTrpLysGluThrGlnGluLysAspProLysGlyTyr

TrpValAsnTyrAsnTyrAspTrpMetPheLysProGlyAlaMetAla

GluValValLysTyrAlaAspGlyValGlyProGlyTrpTyrMetLeu

ValAsnLysGluGluSerLysProAspAsnIleValTyrThrProLeu

ValLysGluLeuAlaGlnTyrAsnValGluValHisProTyrThrVal

ArgLysAspAlaLeuProGluPhePheThrAspValAsnGlnMetTyr

AspAlaLeuLeuAsnLysSerGlyAlaThrGlyValPheThrAspPhe

ProAspThrGlyValGluPheLeuLysGlyIleLys

SEQ ID NO: 2:
MetAspProSerSerHisSerSerAsnMetAlaAsnThrGlnMetLys

SerAspLysIleIleIleAlaHisArgGlyAlaSerGlyTyrLeuPro

GluHisThrLeuGluSerLysAlaLeuAlaPheAlaGlnGlnAlaAsp

TyrLeuGluGlnAspLeuAlaMetThrLysAspGlyArgLeuValVal
```

IleHisAspHisPheLeuAspGlyLeuThrAspValAlaLysLysPhe

ProHisArgHisArgLysAspGlyArgTyrTyrValIleAspPheThr

LeuLysGluIleGlnSerLeuGluMetThrGluAsnPheGluThrLys

AspGlyLysGlnAlaGlnValTyrProAsnArgPheProLeuTrpLys

SerHisPheArgIleHisThrPheGluAspGluIleGluPheIleGln

GlyLeuGluLysSerThrGlyLysLysValGlyIleTyrProGluIle

LysAlaProTrpPheHisHisGlnAsnGlyLysAspIleAlaAlaGlu

ThrLeuLysValLeuLysLysTyrGlyTyrAspLysLysThrAspMet

ValTyrLeuGlnThrPheAspPheAsnGluLeuLysArgIleLysThr

GluLeuLeuProGlnMetGlyMetAspLeuLysLeuValGlnLeuIle

AlaTyrThrAspTrpLysGluThrGlnGluLysAspProLysGlyTyr

TrpValAsnTyrAsnTyrAspTrpMetPheLysProGlyAlaMetAla

GluValValLysTyrAlaAspGlyValGlyProGlyTrpTyrMetLeu

ValAsnLysGluGluSerLysProAspAsnIleValTyrThrProLeu

ValLysGluLeuAlaGlnTyrAsnValGluValHisProTyrThrVal

ArgLysAspAlaLeuProGluPhePheThrAspValAsnGlnMetTyr

AspAlaLeuLeuAsnLysSerGlyAlaThrGlyValPheThrAspPhe

ProAspThrGlyValGluPheLeuLysGlyIleLys

SEQ ID NO: 3:
SerSerHisSerSerAsnMetAlaAsnThr

SEQ ID NO: 4:
LeuProXaaThrGly

---

What is claimed is:

1. An immunogenic composition in a dose having a volume of 0.5 mL comprising a mechanically-sized or a chemically-sized *Streptococcus pneumoniae* serotype 6A capsular polysaccharide having an average size ($M_w$) of between 180-400 kDa conjugated to a carrier protein, and an isolated native *Streptococcus pneumoniae* serotype 6B capsular polysaccharide and an adjuvant, wherein the adjuvant comprises 100-750, 200-500, or 300-400 µg of aluminium as aluminium phosphate.

2. The immunogenic composition according to claim 1 comprising the native *Streptococcus pneumoniae* serotype 6B capsular polysaccharide conjugated to a different carrier protein.

3. The immunogenic composition according to claim 1, wherein the *Streptococcus pneumoniae* serotype 6B capsular polysaccharide has an average size ($M_w$) of between 500-1800, 900-1660, or 1000-1400 kDa.

4. The immunogenic composition according to claim 1, further comprising *Streptococcus pneumoniae* capsular polysaccharide from: (a) serotype 1 having an average size ($M_w$) of between 100-1000, 200-800, 250-600, or 300-400 kDa; (b) serotype 4 having an average size ($M_w$) of between 50-500, 60-300, 70-150, or 75-125 kDa; (c) serotype 5 having an average size ($M_w$) of between 100-1000, 100-700, 100-350, or 150-300 kDa; (d) serotype 7F having an average size ($M_w$) of between 50-1000, 100-750, 150-500, or 200-300 kDa; (e) serotype 9V having an average size ($M_w$) of between 50-1000, 100-750, 150-500, 200-400, or 250-300 kDa; (f) serotype 14 having an average size ($M_w$) of between 50-1000, 100-750, 150-500, or 200-250 kDa; (g) serotype 18C having an average size ($M_w$) of between 50-1000, 50-750, 50-500, 50-190, 50-150 or 80-110 kDa; (h) serotype 19F having an average size ($M_w$) of between 50-1000, 100-750, 100-500, 100-190 or 120-180 kDa; (i) serotype 19A having an average size ($M_w$) of between 50-800 kDa, 110-700, 110-300, 120-200, 130-180, 140-160 or 80-130 kDa; and/or (j) serotype 23F capsular polysaccharide having an average size ($M_w$) of between 500-1500, 600-1500, 700-1300, 900-1250, 800-1100, or 900-1000 kDa.

5. The immunogenic composition according to claim 1 which further comprises *Streptococcus pneumoniae* serotype 22F capsular polysaccharide having an average size ($M_w$) of between 50 and 800 kDa, 110 and 700 kDa, 110-300, 120-200, 130-180, 150-170, 100-190, 100-150, 95-125 or 100-115 kDa.

6. The immunogenic composition according to claim 1 comprising 2, 3, 4, 5 or 6 different carrier proteins.

7. The immunogenic composition according to claim 1 further comprising serotype 19F capsular polysaccharide conjugated to Diphtheria toxoid.

8. The immunogenic composition according to claim 1 wherein the composition further comprises serotype 18C capsular polysaccharide conjugated to tetanus toxoid (TT).

9. The immunogenic composition according to claim 4 further comprising one or more *S. pneumoniae* capsular polysaccharide of serotype 33F, serotype 15, and serotype 12F, conjugated to a carrier protein.

10. A vaccine comprising the immunogenic composition of claim 1 and a pharmaceutically acceptable excipient or a pharmaceutically acceptable carrier.

11. A method for the treatment of *Streptococcus pneumoniae* infection in a subject in need thereof comprising administering to said subject a therapeutically effective amount of the immunogenic composition of claim 4 or the vaccine of claim 10.

12. A method of immunising a human host against *Streptococcus pneumoniae* infection comprising administering to the host an immunoprotective dose of the immunogenic composition of claim 4 or the vaccine of claim 10.

13. A method of inducing an immune response to *Streptococcus pneumoniae* serotype 6A in a subject, the method comprising administering a therapeutically or prophylactically effective amount of the immunogenic composition of claim 4 or the vaccine of claim 10.

14. The immunogenic composition according to claim 1, wherein the dose of the mechanically-sized or the chemically-sized serotype 6A capsular polysaccharide conjugate is between 1 and 10 μg, 1 and 5 μg, or 1 and 3 μg of the capsular polysaccharide.

15. The immunogenic composition according to claim 1, wherein the carrier protein is selected from the group consisting of diphtheria toxoid (DT), CRM197, tetanus toxoid (TT), Fragment C of TT, dPly, PhtA, Put, PhtD, PhtE, PhtDE, OmpC, *Neisseria meningitidis* porin PorB, and *Haemophilus influenzae* Protein D.

16. The immunogenic composition according to claim 1, wherein the mechanically-sized or the chemically-sized *Streptococcus pneumoniae* serotype 6A capsular polysaccharide is conjugated to the carrier protein via a linker or directly conjugated to the carrier protein.

17. The immunogenic composition according to claim 16, wherein the mechanically-sized or the chemically-sized *Streptococcus pneumoniae* serotype 6A capsular polysaccharide is conjugated to the carrier protein or to the linker using CDAP chemistry or conjugated to the carrier protein or to the linker using reductive amination.

\* \* \* \* \*